US006365796B1

(12) United States Patent
Lowell et al.

(10) Patent No.: US 6,365,796 B1
(45) Date of Patent: Apr. 2, 2002

(54) TRANSGENIC UCP2 KNOCKOUT MOUSE AND USE THEREOF

(75) Inventors: Bradford B. Lowell, Southborough; Chen-Yu Zhang, Somerville, both of MA (US); Catherine B. Chan, Prince Edward Island; Michael B. Wheeler, Toronto, both of (CA)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 09/505,298

(22) Filed: Feb. 16, 2000

(51) Int. Cl.$^7$ ............... G01N 33/00; A01K 67/027; C12N 15/00; C12N 5/06; C12Q 1/54
(52) U.S. Cl. ................ 800/3; 800/18; 800/25; 800/21; 435/14; 435/325; 435/455; 435/463
(58) Field of Search ................. 800/14, 18, 21, 800/3, 25; 435/455, 463, 320.1, 14, 325, 461

(56) References Cited

FOREIGN PATENT DOCUMENTS

| WO | WO 98/31396 | 7/1998 |
|---|---|---|
| WO | WO 88/00123 | 1/1999 |
| WO | WO 99/07358 | 2/1999 |
| WO | WO 99/48905 | 9/1999 |
| WO | WO 99/53953 | 10/1999 |
| WO | WO 99/64458 | 12/1999 |

OTHER PUBLICATIONS

Fleury, C., et al., "Uncoupling protein–2: a novel gene linked to obesity and hyperinsulinemia," *Nat. Genet.*, 15:269–272 (1997).
Kaisaki, P.J., et al., "Localization of tub and uncoupling proteins (Ucp) 2 and 3 to a region of rat Chromosome 1 linked to glucose intolerance and adiposity in the Goto–Kakizaki (GK) Type 2 diabetic rat," *Mammalian Genome*, 9:910–912 (1998).
Pecquer, C., et al., "Functional Organization of the Human Uncoupling Protein–2 Gene, and Juxtaposition to the Uncoupling Protein–3 Gene," *Biochemical and Biophysical Research Communications*, 255:40–46 (1999).
Wang, M.Y., et al., "Adenovirus–Mediated Overexpression of Uncoupling Protein–2 in Pancreatic Islets of Zucker Diabetic Rats Increases Oxidative Activity and Improves β–Cell Function," *Diabetes*, 48:1020–1025 (1999).
Fleury, C., et al., "The mitochondrial uncoupling protein–2: current status," *Int. J. Biochem. Cell. Biology*, 31 (10): 1261–1278 (1999).
Jabůrek, M., et al., "Transport Function and Regulation of Mitochondrial Uncoupling Proteins 2 and 3," *J. Biol. Chem.*, 274 (37) :26003–26007 (1999).
Chan, C.B., et al., "Overexpression of Uncoupling Protein 2 Inhibits Glucose–Stimulated Insulin Secretion From Rat Islets," *Diabetes*, 48:1482–1486 (1999).

Yamada, M., et al., "Genomic organization and promotor function of the mouse uncoupling protein 2 (UCP2) gene," *FEBS Letters*, 432:65–69 (1998).
Gimeno, R.E., et al., "Cloning and Characterization of an Uncoupling Protein Homolog; A Potential Molecular Mediator of Human Thermogenesis," *Diabetes*, 46:900–906 (1997).
Rial, E., et al., "Retinoids activate proton transport by the uncoupling proteins UCP1 and UCP2," *EMBO Journal*, 18 (21) :5827–5833 (1999).
Gong et.al. ; Lack of Obesity and Normal Response to Fasting and Thyroid Hormone in Mice Lacking Uncoupling Protein–3, 2000, The Journal of Biological Chemistry, vol. 275 No. 21: 16251–16257.*
Mullins et. al.; Perspective Series: Molecular Medicine in Genetically Engineered Animals; 1996,J. Clin. Invest. vol. 98: S37–S40.*
Moreadith et. al.; Gene Targeting in embryonic stem cells: the new physiology and metabolism, 1997, J. Moi Med 75: 208–216.*
Seamark; Progress and Emerging Problems in Livestockl Transgenesis: a Summary Perspective, 1994, Reprod Fertil. Dev. 6: 653–657.*
Boss, O. *et al.*, "The uncoupling proteins, a review proteins, a review,", *Eur. J. Endocrinol.* 139:1–9 (1998).
Arsenijevic, D. *et al.*, "Disruption of the uncoupling protein–2 gene in mice reveals a rolein immunitiy ans reacitve oxygen speecies production,"*Nature Genet*, 26:435–439 (2000).
Vidal–Puig, Antonio, J. "Uncoupling exepctations."*Nature Genet.*, 26:387–388 (2000).
Zhang, C. *et al.*, "Uncoupling Protein–2 Negatively Regulates Insulin Secretion and Is A Major Link between Obesity, ; 62 Cell Dysfunictional, and Type 2 Diabetes," *Cell* 105:745–755 (2001).
Enerback, S. *et al.*, "Mack lacking mithochondrial uncoupling protein are cold–sensitive but not obesse,"*Nature* 387:90–94 (1997).

(List continued on next page.)

*Primary Examiner*—Dave T. Nguyen
*Assistant Examiner*—Quang Nguyen
(74) *Attorney, Agent, or Firm*—Hamilton, Brook, Smith & Reynolds, P.C.

(57) ABSTRACT

The present invention provides a transgenic non-human mammal which lacks a functional UCP2 gene. The UCP-2 deficient transgenic knockout mammal described herein provides a source of cells and animals useful to practice methods for the identification and/or evaluation of agents for their ability to affect signaling in cells, such as pancreatic β-cells, in which ATP serves a regulatory function. Further aspect of the invention provide a method for the identification of agents (e.g., therapeutic agents) which inhibit UCP2 activity; a method for the identification of agents which mimic UCP2 activity and a method of treating diseases or conditions associated with UCP2 function (e.g., negative regulation or uncoupling activity).

15 Claims, 14 Drawing Sheets

OTHER PUBLICATIONS

Kimura, K. et al., "Induction of uncoupling protein (UCP) 2 in primary cultured hepatocytes," *FEBS Lett.* 457:75–79 (1999).

Shimabukuro, M. et al., "Induction of Uncoupling Protein–2 mRNA by Troglitazone in the Pancreatic Islets of Zucker Diabetic Fatty Rats," *Biochem. Biophys. Res. Commun.*, 237:359–361 (1997).

Baumruk, F. et al., "Transgenic UCP1 in white adipocytes modulates mitochondrial membrane potential," *FEBS Lett.* 44:206–210 (1999).

* cited by examiner

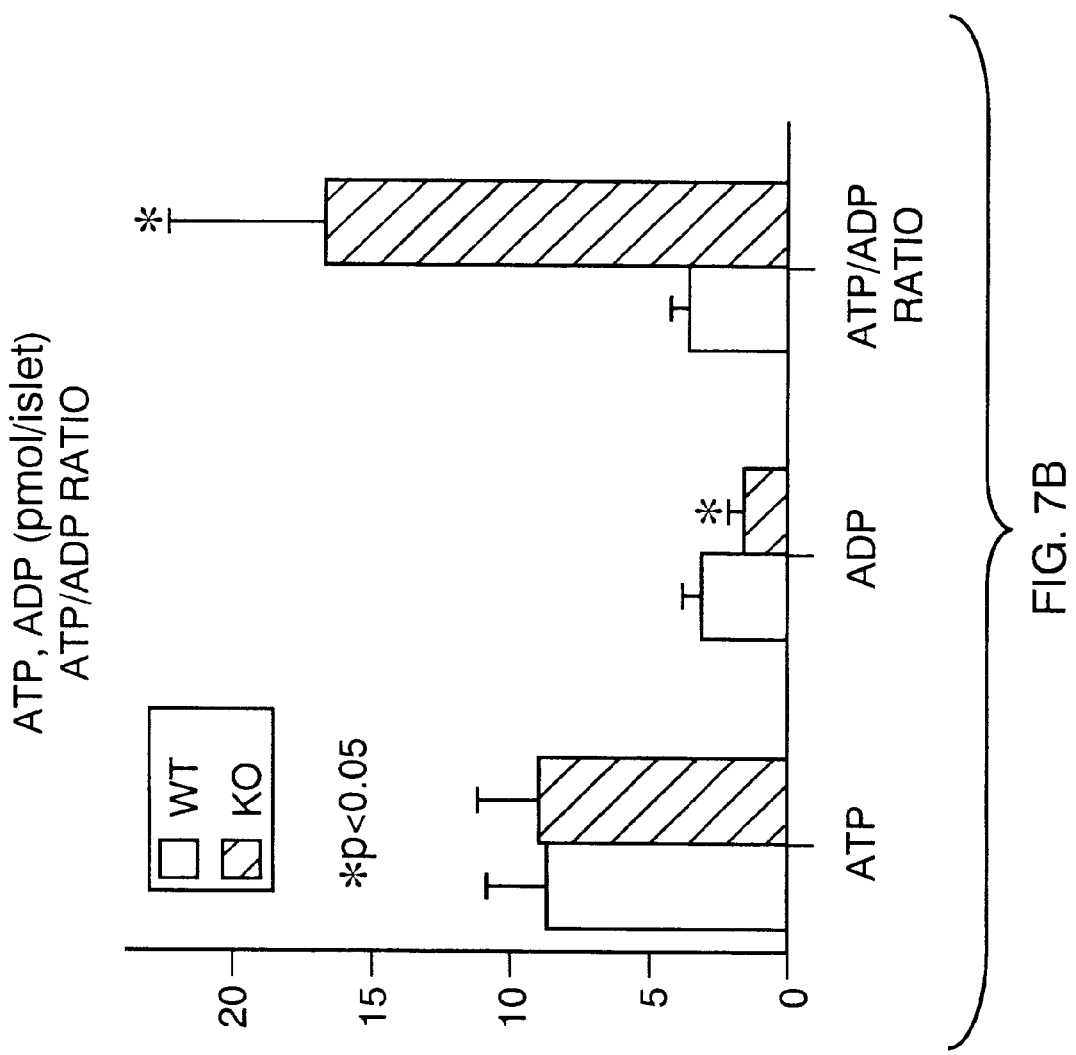

TRANSGENIC UCP2 KNOCKOUT MOUSE AND USE THEREOF

GOVERNMENT SUPPORT

The invention was supported, in whole or in part, by a grant NIH (RO1 DK53477) from the National Institute for Health. The Government has certain rights in the invention.

BACKGROUND OF THE INVENTION

Uncoupling protein 2 (UCP2) (Fleury, C., et al., *Nat. Genet,* 15:269 (1997); Gimeno, R. E., et al., *Diabetes,* 46:900 (1997)) and uncoupling protein 3 (UCP3) (Boss, O., et al., *FEBS Lett.,* 408:39 (1997); Vidal-Puig, A., et al., *Biochem. Biophys. Res. Commun.,* 235:79 (1997); Gong, D. W., et al., *J. Biol. Chem.* 272:24129 (1997)) are recently discovered members of the mitochondrial inner membrane carrier family with high homology to UCP1 (Nicholls, D. G., et al., *Physiol. Rev.,* 64:1 (1984); Klingenberg, M., and Huang, S. G., *Biochim. Biophys. Acta.,* 1415:271 (1999)) and expression patterns which are consistent with the hypothesis that they play a role in the regulation of cellular processes in which ATP plays a regulatory function. Consistent with this theory, studies in which UCP2 and UCP3 have been overexpressed in yeast (Rial, E., et al., *EMBO J,* 18:5827 (1999); Hinz, W., et al., *FEBS Lett,* 448:57 (1999); C. Y Zhang, et al., *FEBS Lett,* 449:129 (1999)) or reconstituted into proteoliposomes (Jaburek, M., et al., *J Biol. Chem.,* 274:26003 (1999)) indicate a proton leak (and as a consequence modulator of ATP) role for these new UCPs. UCP3 is expressed primarily in skeletal muscle where it likely plays a role in regulated thermogenesis. In contrast, UCP2 has a nearly ubiquitous expression pattern, but at varying levels in a number of tissues and cell types including tissues involved in glucose homeostasis (pancreatic islets, white fat, brown fat, heart, skeletal muscle). For example, UCP2 mRNA (Zhou, Y. T., et al., *Proc. Natl. Acad. Sci. U.S.A.,* 94:6386 (1997); Chan, C. B., et al., *Diabetes* 48:1482 (1999)) and protein are highly expressed in pancreatic β-cells.

β-cell function deteriorates in many individuals with obesity and insulin resistance, culminating in the development of type II diabetes mellitus. UCP2 mRNA expression is increased in adipose tissue of ob/ob obese mice, raising the possibility that it may also be increased in β-cells as well. If true, obesity-induced UCP2 expression in β-cells could contribute to β-cell dysfunction, promoting the development of diabetes. Consistent with this theory, it has been reported that UCP2 lies within a major quantitative trait loci (QTL) (murine chromosome 7; rat chromosome 1 and human chromosome 11) controlling diet-induced hyperinsulinemia in C57B1/6 mice (Fleury, C., et al., *Nat. Genet,* 15:269 (1997); Seldin, M. F., et al., *J. Clin. Invest.,* 94:269 (1994)); glucose intolerance and adiposity in the GK (Goto-Kakizaki) model of type 2 diabetes the rat (Gauguier, D., et al., *Nat. genet.,* 12:38 (1996); Galli, J., et al., *Nat. genet.,* 12:31 (1996); Kaisaki, P. J., et al., *Mamm. genome,* 9:910 (1998)), and human insulin-dependent diabetes locus-4 (Fleury, C., et al., *Nat. Genet,* 15(3):269–272 (1997)). Unfortunately, little is known about regulation of β-cell UCP2 gene expression during the pathogenesis of NIDDM. Similarly, little is known about regulators of UCP2 activity, which could also be altered, contributing to β-cell dysfunction.

Thus, additional studies, particularly in vivo studies, are needed to elucidate the biochemical physiological functions of UCP2 and to identify molecular targets, regulators and therapeutic strategies for the treatment or prevention of diseases or conditions associated with UCP2-regulated cellular processes.

SUMMARY OF THE INVENTION

The present invention relates to a transgenic non-human mammal (e.g., mouse) which lacks a functional UCP2 gene (also referred to herein as transgenic non-human UCP2 knockout mammal or a UCP2 knockout mammal). The transgenic non-human mammal of the present invention can have at least one non-functional allele for the UCP2 gene. In one embodiment, the transgenic non-human mammal is characterized by a disruption of the UCP2 gene which is either a homozygous disruption or a heterozygous disruption. In a particular embodiment, the genome of the UCP2 knockout mammal comprises a disruption of a segment between introns 2 and 7 of the UCP2 gene. In another embodiment, the genome of the UCP2 knockout mammal comprises an insertion of an exogenous nucleic acid sequence into an exon of the UCP2 gene.

As a result of the disruption of the UCP2 gene, the transgenic knockout mammal of the present invention manifests a particular phenotype. In one embodiment, the UCP2 knockout mammal has altered insulin/glucose homeostasis. In a particular embodiment, the transgenic non-human mammal is characterized by increased glucose-stimulated insulin secretion.

The invention further provides a method of producing a transgenic non-human mammal which lacks a functional UCP2 gene. In this method, a targeting vector is introduced into an embryonic stem cell to produce a transgenic stem cell in which the UCP2 gene is disrupted. A transgenic embryonic stem cell which includes a disrupted UCP2 gene due to the integration of the targeting vector into its genome is then selected. The selected embryonic stem cell is introduced into a blastocyst, thereby forming a chimeric blastocyst; and the chimeric blastocyst is introduced into the uterus of a pseudopregnant mammal wherein the pseudopregnant mammal gives birth to a transgenic non-human mammal which lacks a functional UCP2 gene due to heterozygous disruption of the UCP2 gene. The method can further comprise breeding the transgenic non-human mammal which lacks a functional UCP2 gene due to a heterozygous disruption with a second mammal of the same species to generate F1 progeny having a heterozygous disruption of the UCP2 gene, thereby expanding the population of mammals having a heterozygous disruption of the UCP2 gene. The F1 progeny are then crossbred to produce a transgenic non-human mammal which lacks a functional UCP2 gene due to a homozygous disruption of the UCP2 gene.

The present invention also relates to constructs or vectors (e.g., UCP2 targeting construct) designed to disrupt the function of a wild type mammalian UCP2 gene. In one embodiment, the invention provides a construct which comprises about 5.5 kb of a UCP2 sequence which is 5' of an expression cassette. In a particular embodiment, the construct comprises 8.7 kb of genomic UCP2 sequence wherein 5.5 kb of the 8.7 kb genomic sequence is 5' of an expression cassette and 3.2 kb of the 8.7 kb genomic sequence is 3' of the expression cassette. More specifically, the invention provides a UCP2 gene replacement vector in which the genomic nucleotide sequence of the UCP2 gene between introns 2 and 7 is removed and/or replaced with a PGK-Neo-Poly(A) expression cassette.

The present invention also provides cells, cell lines, mammalian tissues, cellular extracts, organelles (e.g., mitochondria) and organs which lack a functional UCP2 gene. In one embodiment, the cells are pancreatic beta cells.

The cells, cell lines, mammalian tissues, cellular extracts, organelles (e.g., mitochondria) and organs of the instant invention can be used in a method for determining whether an agent inhibits UCP2. For example, pancreatic tissue, islets or cells isolated from wild-type mouse and a UCP2 knockout mouse can be used in combination to identify an agent which inhibits UCP2-mediated negative regulation of β-cell secretion of insulin. In one embodiment, a suitable in vitro screening method comprises combining cells which comprise a wild type UCP2 gene (wild type cells), an amount of glucose sufficient to stimulate insulin production and the agent; and combining cells which lack a functional UCP2 gene (UCP2 knockout cells), an amount of glucose sufficient to stimulate insulin production of the cells and the agent. The cells are maintained under conditions appropriate to stimulate insulin production. The amount of insulin produced by the wild type cells is compared to the amount of insulin produced by the UCP2 knockout cells, wherein if the amount of insulin produced by the wild type cells is increased compared to the amount of insulin produced by the knockout cells, then the agent inhibits UCP2.

The in vitro screening method can further comprise the use of any suitable control. For example, in one embodiment, the in vitro screening method can further comprise combining the wild type cells with an amount of glucose sufficient to stimulate insulin production in the absence of the agent; and combining UCP2 knockout cells with an amount of glucose sufficient to stimulate insulin production in the absence of the agent. The cells are maintained under conditions appropriate to stimulate insulin production. The amount of insulin produced by the wild type cells in the presence of the agent is compared to the amount of insulin produced by the wild type cells in the absence of the agent; and the amount of insulin produced by the UCP2 knockout cells in the presence of the agent is compared to the amount of insulin produced by the UCP2 knockout cells in the absence of the agent. If the amount of insulin produced by the wild type cells in the presence of the agent is increased compared to the amount of insulin produced by the wild type cells in the absence of the agent, and the amount of insulin produced by the UCP2 knockout cells in the presence of the agent is similar to the level produced by the knockout cells in the absence of the agent, then the agent inhibits UCP2. According to the instant invention, an appropriate pancreatic β-cell based assay for the identification of agents which inhibit UCP2-mediated regulation of insulin secretion can be practiced with cells characterized by a disruption of the UCP2 gene selected from the group consisting of: a homozygous disruption and a heterozygous disruption.

Alternatively, a high through-put screening assay for the identification of agents which modulate (e.g., inhibit or activate) UCP2 activity can be established based on the knowledge that UCP2 effects ATP/ADP ratios. For example, cells (or cell lines) comprising a disrupted UCP2 gene which have either been derived from the transgenic non-human UCP2 knockout mammals described herein, or genetically engineered by the gene targeting method described herein can be transfected with a reporter gene, such as a luciferase expression construct designed to emit a luminescence signal that is directly correlated to ATP concentration (Kohler, M., et al., *FEBS Lett.*, 441:97–102 (1998) and Kennedy, H. J., et al., *JBC*, 274:13281–91 (1999)). The resulting cells can then be contacted with various agents which are being evaluated for their ability to modulate (e.g., inhibit or enhance) UCP2 activity. Modulators of UCP2 activity can be identified by comparing the luminescence signal of cells expressing a wild-type UCP2 with the signal of cells whose genome comprises a disrupted UCP2 gene. A UCP2 specific agent can be determined by identifying agents which modulate the ATP level of cells comprising wild-type UCP2 gene relative to the ATP level of control cells, but which do not effect the ATP level of cells comprising a disrupted UCP2 gene. Based on the knowledge that ATP/ADP ratios control insulin secretion in pancreatic β-cells, it is also reasonable to assume that the class of UCP2-specific agents identified in the above described assay can be used to control insulin secretion.

Another embodiment of the present invention provides an in vivo screening method for determining whether an agent inhibits UCP2. The increased glucose-sensitivity of the transgenic non-human UCP2 knockout mammals of the instant invention can be utilized as the basis of a screening assay in which an agent that is being evaluated for its ability to inhibit the UCP2-mediated negative regulation of insulin production in response to glucose stimulation. In one embodiment, a suitable in vivo screening method comprises administering to a non-human mammal which comprises a wild type UCP2 gene (wild type mammal), an amount of glucose sufficient to stimulate insulin production and the agent; and combining a transgenic non-human mammal which lacks a functional UCP2 gene (UCP2 knockout mammal), an amount of glucose sufficient to stimulate insulin production of the cells and the agent. The amount of insulin produced by the mammals is measured. The amount of insulin produced by the wild type mammal is compared to the amount of insulin produced by the UCP2 knockout mammal. If the amount of insulin produced by the wild type mammal is increased compared to the amount of insulin produced by the knockout mammal, then the agent inhibits UCP2.

The in vivo screening method can further comprise the use of any suitable control. For example, in one embodiment, the in vivo screening method can further comprise administering to a wild type mammal an amount of glucose sufficient to stimulate insulin production in the absence of the agent; and administering to a UCP2 knockout mammal an amount of glucose sufficient to stimulate insulin production in the absence of the agent. The amount of insulin produced by the mammals is measured. The amount of insulin produced by the wild type mammal in the presence of the agent is compared to the amount of insulin produced by the wild type mammal in the absence of the agent; and the amount of insulin produced by the UCP2 knockout mammal in the presence of the agent is compared to the amount of insulin produced by the UCP2 knockout mammal in the absence of the agent. If the amount of insulin produced by the wild type mammal in the presence of the agent is increased compared to the amount of insulin produced by the wild type mammal in the absence of the agent, and the amount of insulin produced by the UCP2 knockout mammal in the presence of the agent is similar to the level produced by the knockout mammal in the absence of the agent, then the agent inhibits UCP2.

Also encompassed by the present invention is an method of identifying an agent which mimics UCP2 activity. In one embodiment, the method comprises introducing the agent (e.g., potential UCP2 mimic) into cells which lack a functional UCP2 gene and determining whether a UCP2-mediated cellular function (one or more) occurs in the presence of the agent. If UCP2-mediated cellular function occurs in the cells which lack a functional UCP2 gene in the presence of the agent, then the agent is a UCP2 mimic.

In another embodiment, the method of identifying an agent which mimics UCP2 activity comprises introducing the agent into a transgenic non-human mammal which lacks a functional UCP2 gene and determining whether a UCP2-mediated cellular function (one or more) occurs in the presence of the agent. If UCP2-mediated cellular function occurs in the transgenic non-human mammal which lacks a functional UCP2 gene in the presence of the agent, then the agent is a UCP2 mimic.

In the method of identifying a UCP2 mimic, examples of a (one or more) UCP2-mediated cellular function includes, for example, altered insulin/glucose homeostasis and responsiveness to glucose stimulation, altered mitochondrial activity, decreased responsiveness to glucose-stimulation, decreased level of insulin production, decreased ambient fed-state serum insulin levels combined with a decreased glucose level.

The present invention also relates to methods of treatment or prevention of conditions (e.g., hyperglycemia) or diseases (e.g., type 2 diabetes) associated with aberrant UCP2 function (e.g., negative regulation or uncoupling activity). In one embodiment the invention provides a method of increasing insulin production in an individual comprising administering to the individual an agent which inhibits UCP2 activity. In another embodiment, the invention provides a method of decreasing blood glucose in an individual comprising administering to the individual an agent which inhibits UCP2 activity. The invention further provides a method of treating diabetes (e.g., type 2 diabetes; non-insulin dependent diabetes mellitus) in an individual comprising administering to the individual an agent which inhibits UCP2 activity. An alternative embodiment of this aspect of the invention further provides a method of modulating mammalian mitochondrial activity (e.g., respiration rates and inner mitochondrial membrane potential). In one embodiment, the invention provides a method of coupling mitochondria (e.g., cellular respiration and ATP production) in an individual comprising administering to the individual an agent which inhibits UCP2 activity. Alternatively, the present invention relates to a method of enhancing the uncoupling of cellular respiration and ATP production in an individual comprising administering to the individual an agent which enhances (activates, induces) UCP2 activity.

Thus, the invention provides a source of cells and animals useful for elucidating the function of UCP2 in intact animals whose genomes comprise a wild-type UCP2 gene. In addition, Applicants have discovered that UCP2 negatively regulates insulin production in animals and uncouples mitochondrial respiration. Further aspects of the invention provide a method for the identification of agents (e.g., therapeutic agents) which inhibit UCP2 activity; and a method of treating diseases or conditions associated with UCP2 function (e.g., negative regulation or uncoupling activity).

BRIEF DESCRIPTION OF THE DRAWINGS

FIG. 7B is a graphic representation demonstrating the ATP and ADP levels (pmol/islet) and ATP/ADP ratios of pancreatic islets from wild type (+/+) and UCP2 knockout (–/–) mice after two hour exposure to 5.5 mM glucose.

DETAILED DESCRIPTION OF THE INVENTION

Figure 1A:
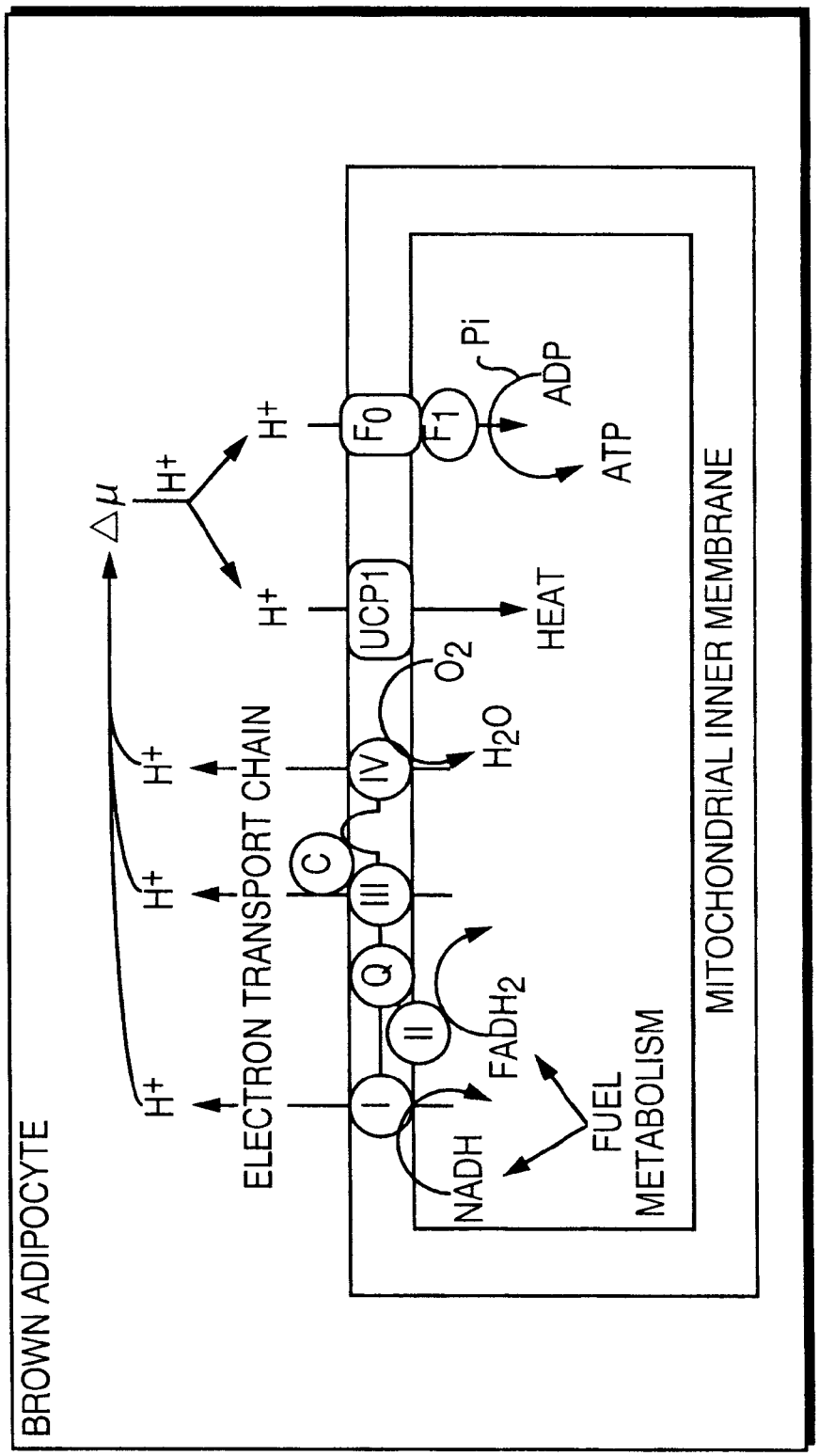
FIG. 1A is a schematic representation of the role played by UCP1 in regulating heat production by brown adipocytes.

The present invention provides a transgenic non-human mammal which lacks a functional UCP2 gene referred to herein as a "transgenic non-human UCP2 knockout mammal" or a "UCP2 knockout mammal". In a particular embodiment, the genome of the UCP2 knockout mammal comprises at least one non-functional allele for the endogenous UCP2 gene. Thus, the invention provides a source of cells (e.g., tissue, cells, cellular extracts, organelles) and animals useful for elucidating the function of UCP2 in intact animals whose genomes comprise a wild-type UCP2 gene. In addition, Applicants have discovered that UCP2 negatively regulates insulin production in animals and uncouples mitochondrial respiration and ATP production. Further aspects of the invention provide a method for the identification of agents (e.g., therapeutic agents) which inhibit or mimic UCP2 activity; and a method of treating diseases or conditions associated with UCP2 function (e.g., negative regulation or uncoupling activity).

Any suitable mammal can be used to produce the UCP2 knockout mammal described herein. For example, a suitable mammal can be, a mouse (mice), a rat, a rabbit, a pig, a sheep or a cow.

As used herein, the term "gene" refers to DNA sequences which encode the genetic information (e.g., nucleic acid sequence) required for the synthesis of a single protein (e.g., polypeptide chain). The term "UCP2 gene" refers to a particular mammalian gene which comprises a DNA sequence which encodes UCP2. An "allele" is an alternative from of gene found at the same locus of a homologous chromosome. Homologous chromosomes are chromosomes which pair during meiosis and contain identical loci. The term locus connotes the site (e.g., location) of a gene on a chromosome.

Published studies reporting the structure of the murine and human UCP2 genes indicate that both genes contain eight exons and seven introns (Yamada, M., et al., *FEBS Lett.*, 432:65–69 (1998); Argyropoulos, G., et al., *Diabetes*, 47(4):685–687 (1998); Pecqueor, C., et al., *Biochem. Biophys. Res. Common.*, 255:40–46 (1999); and Surwit, R. S., et al., *Proc. Natl. Acad. Sci. U.S.A.*, 95(7):4061–4065 (1998) and that the transcriptional unit is composed of two non-coding exons followed by six exons comprising the genomic nucleotide sequence which encodes the UCP2 protein. The murine gene spans a 6.3 kb region on chromosome 7, and the human gene spans an 8.4 kb region on chromosome 11.

As used herein the terms "transgenic non-human UCP2 knockout mammal" and "UCP2 knockout mammal" refer to a mammal whose genome comprises a disrupted or inactivated UCP2 gene. Those of skill in the art will recognize that the term "knockout" refers to the functional inactivation of the gene. The disruption introduces a chromosomal defect (e.g., mutation or alteration) in the UCP2 gene at a point in the nucleic acid sequence that is important to either the expression of the UCP2 gene or the production of a functional UCP2 protein (e.g., polypeptide). Thus, the introduction of the disruption inactivates the endogenous target gene (e.g., UCP2 gene).

As used herein the terms "disruption", "functional inactivation", "alteration" and "defect" connote a partial or complete reduction in the expression and/or function of the UCP2 polypeptide encoded by the endogenous gene of a single type of cell, selected cells (e.g, pancreatic β-cells) or all of the cells of a non-human transgenic UCP2 knockout animal. Thus, according to the instant invention the expression or function of the UCP2 gene product can be completely or partially disrupted or reduced (e.g., by 50%, 75%, 80%, 90%, 95% or more) in a selected group of cells (e.g., a tissue or organ) or in the entire animal. As used herein the term "a functionally disrupted UCP2 gene" includes a modified UPC2 gene which either fails to express any polypeptide product or which expresses a truncated protein having less than the entire amino acid polypeptide chain of a wild-type protein and is non-functional (partially or completely non-functional).

Disruption of the UCP2 gene can be accomplished by a variety of methods known to those of skill in the art. For example, gene targeting using homologous recombination, mutagenesis (e.g., point mutation) and antisense technology can be used to disrupt a UCP2 gene.

More specifically, the invention provides a transgenic knockout mammal whose genome comprises either a homozygous or heterozygous disruption of its UCP2 gene. A knockout mammal whose genome comprises a homozygous disruption is characterized by somatic and germ cells which contain two nonfunctional (disrupted) alleles of the UCP2 gene while a knockout mutant whose genome comprises a heterologous disruption is characterized by somatic and germ cells which contain one wild-type allele and one nonfunctional allele of the UCP2 gene.

As used herein, the term "genotype" refers to the genetic makeup of an animal with respect to the UCP2 chromosomal locus. More specifically the term genotype refers to the status of the animal's UCP2 alleles, which can either be intact (e.g., wild-type or +/+); or disrupted (e.g., knockout) in a manner which confers either a heterozygous (e.g., +/–); or homozygous (–/–) knockout genotype.

The present invention also provides methods of producing a transgenic non-human mammal which lacks a functional UCP2 gene. Briefly, the standard methodology for producing a transgenic embryo requires introducing a targeting construct, which is designed to integrate by homologous recombination with the endogenous nucleic acid sequence of the targeted gene, into a suitable embryonic stem cells (ES). The ES cells are then cultured under conditions effective for homologous recombination (i.e., of the recombinant nucleic acid sequence of the targeting construct and the genomic nucleic acid sequence of the host cell chromosome). Genetically engineered stem cell that are identified as comprising a knockout genotype which comprises the recombinant allele is introduced into an animal, or ancestor thereof, at an embryonic stage using standard techniques which are well known in the art (e.g., by microinjecting the genetically engineered embryonic stem (ES) cell into a blastocyst). The resulting chimeric blastocyst is then placed within the uterus of a pseudo-pregnant foster mother for the development into viable pups. The resulting viable pups include potentially chimeric founder animals whose somatic and germline tissue comprise a mixture of cells derived from the genetically-engineered ES cells and the recipient blastocyst. The contribution of the genetically altered stem cell to the germline of the resulting chimeric mice allows the altered ES cell genome which comprises the disrupted target gene to be transmitted to the progeny of these founder animals thereby facilitating the production of transgenic "knockout animals" whose genomes comprise a gene which has been genetically engineered to comprise a particular defect in a target gene.

In a particular embodiment of the present invention, a transgenic UCP2 knockout mammal is produced by introducing a targeting vector which disrupts the UCP2 gene into an embryonic stem cell thereby producing a transgenic stem cell. A transgenic embryonic stem cell which includes the disrupted UCP2 gene due to the integration of the targeting vector into its genome is selected and introduced into a blastocyst, thereby forming a chimeric blastocyst. The chimeric blastocyst is introduced into the uterus of a pseudopregnant mammal wherein the pseudopregnant mammal gives birth to a transgenic non-human mammal which lacks a functional UCP2 gene.

As a result of the disruption of the UCP2 gene, the UCP2 knockout mammal of the present invention can manifest a particular phenotype. The term phenotype refers to the resulting biochemical or physiological consequences attributed to a particular genotype. In one embodiment, the UCP2 knockout mammal has altered insulin/glucose homeostasis and responsiveness to glucose stimulation. In another embodiment, the UCP2 knockout mammal has altered mitochondrial activity (e.g., respiration rates and inner mitochondrial membrane potential). In an alternative embodiment, the UCP2 knockout mammal has an increased responsiveness to glucose-stimulation, and, as a result, releases an increased level of insulin relative to the amount of insulin released by an appropriate control mammal (e.g., wild-type) in response to the same glucose challenge. In another embodiment, the altered insulin/glucose homeostasis is manifest as an increased ambient fed-state serum insulin level combined with a decreased glucose level. In an alternative embodiment, the phenotype is manifest as an increased ambient fasting-state insulin level in combination with a blood glucose level that is not significantly different from the ambient blood glucose level of a control mammal. In another embodiment, the phenotype of the UCP2 knockout mammal manifests a faster glucose clearance time in response to a standard glucose tolerance test. In another embodiment, the UCP2 knockout mammal has increased ATP levels and ATP/ADP ratio in appropriate indicator cells. As used herein the term indicator cells refers to a cell (e.g., cell line, tissue, cellular extract, or organelle) which performs a cellular function that can be measured or quantified (e.g., insulin production, respiration, ATP synthesis, proton transport or the establishment of an electrochemical gradient). In yet another embodiment of the invention, the phenotype of the UCP2 knockout mammal has a decreased level of proton leak (e.g., uncoupling) in the mitochondria of its cells relative to the level of proton leak in the mitochondria of wild-type control cells. This embodiment can also be characterized as demonstrating an increased ratio of state 3 (presence of ADP)/state 4 (absence of ADP respiration.

One of skill in the art will easily recognize that the UCP2 gene can be disrupted in a number of different ways, any one of which may be used to produce the UCP2 knockout mammals of the present invention. For example, a transgenic knockout animal according to the instant invention can be produced by the method of gene targeting. As used herein the term "gene targeting" refers to a type of homologous recombination which occurs as a consequence of the introduction of a targeting construct (e.g., vector) into a mammalian cell (e.g., an ES cell) which is designed to locate and recombine with a corresponding portion of the nucleic acid sequence of the genomic locus targeted for alteration (e.g., disruption) thereby introducing an exogenous recombinant nucleic acid sequence capable of conferring a planned alteration to the endogenous gene. Thus, homologous recombination is a process (e.g., method) by which a particular DNA sequence can by replaced by an exogenous genetically engineered sequence. More specifically, regions of the targeting vector which have been genetically engineered to be homologous ( e.g., complimentary) to the endogenous nucleotide sequence of the gene which is targeted for disruption line up or recombine with each other such that the nucleotide sequence of the targeting vector is incorporated into (e.g, integrates with) the corresponding position of the endogenous gene.

Figure 2:
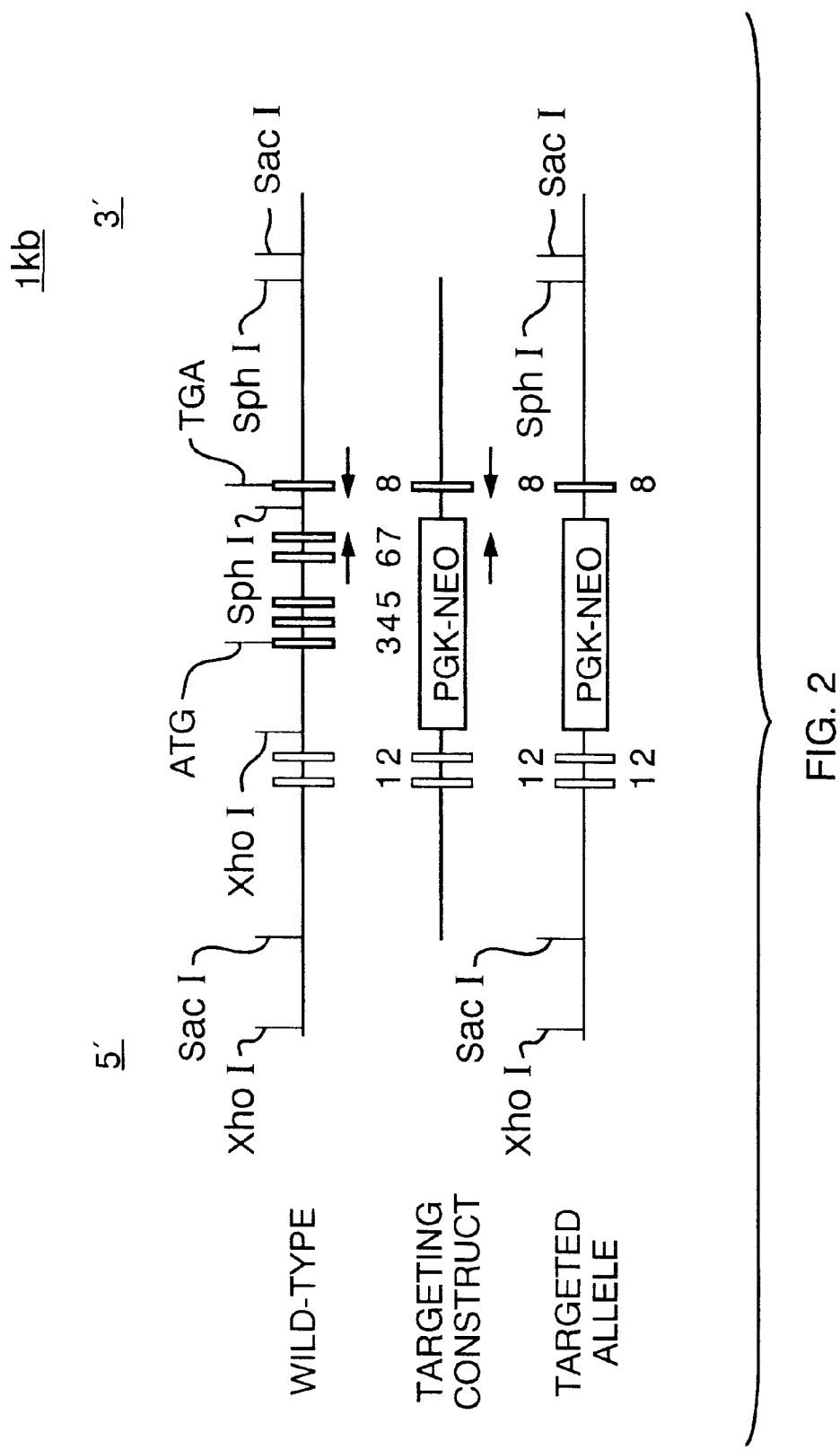
FIG. 2 is a schematic representation of the wild-type UCP2 allele (top), the UCP2 gene targeting construct (middle) and the targeted UCP2 allele after homologous recombination and disruption of the endogenous UCP2 gene (bottom); filled boxes refer to exons corresponding to coding sequence, the locations of which have been previously published; arrow refers to the orientation of transcription of the PGK-NEO cassette.

One embodiment of the present invention provides a vector construct (e.g., a UCP2 targeting vector or UCP2 targeting construct) designed to disrupt the function of a wild-type (endogenous) mammalian UCP2 gene. In general terms, an effective UCP2 targeting vector comprises a recombinant sequence that is effective for homologous recombination with the UCP2 gene. For example, a replacement targeting vector comprising a genomic nucleotide sequence which is homologous to the target sequence operably linked to a second nucleotide sequence which encodes a selectable marker gene exemplifies an effective targeting vector. Integration of the targeting sequence into the chromosomal DNA of the host cell (e.g., embryonic stem cell) as a result of homologous recombination introduces an intentional disruption, defect or alteration (e.g., insertion, deletion) into the sequence of the endogenous gene. One aspect of the present invention is to replace all or part of the nucleotide sequence of a non-human mammalian gene which encodes the UCP2 polypeptide. In a particular embodiment, exons 3, 4, 5, 6 and/or 7 of the UCP2 gene are disrupted. In another embodiment, a segment between introns 2 and 7, including the start codon of the UCP2 gene, is removed. As described in Example 1, a target construct in which a segment between introns 2 and 7 of the UCP2 gene is removed and replaced with a PGK-NEO-Poly(A) expression cassette. FIG. 2 presents a graphic representation of this UCP2 targeting vector which is demonstrated herein to be effective for disrupting the mouse UCP2 gene.

One of skill in the art will recognize that any UCP2 genomic nucleotide sequence of appropriate length and composition to facilitate homologous recombination at a specific site that has been preselected for disruption can be employed to construct a UCP2 targeting vector. Guidelines for the selection and use of sequences are described for example in Deng and Cappecchi, *Mol. Cell. Biol.*, 12:3365–3371 (1992) and Bollag, et al., *Annu. Rev. Genet.*, 23:199–225 (1989). For example, a wild-type UCP2 gene can be mutated and/or disrupted by inserting a recombinant nucleic acid sequence (e.g., a UCP2 targeting construct or vector) into all or a portion of the UCP2 gene locus. For example, a targeting construct can be designed to recombine with a particular portion within the enhancer, promoter, coding region, start codon, noncoding sequence, introns or exons of the UCP2 gene. Alternatively, a targeting construct can comprise a recombinant nucleic acid which is designed to introduce a stop codon after exon 2, 3, 4, 5, 6 and/or 7 of the UCP2 gene.

Suitable targeting constructs of the invention can be prepared using standard molecular biology techniques known to those of skill in the art. For example, techniques useful for the preparation of suitable vectors are described by Maniatis, et al., Molecular Cloning: A Laboratory Manual, Cold Spring Harbor Laboratory, Cold Spring Harbor, N.Y.; which disclosures are hereby incorporated by reference. Appropriate vectors include a replacement vector such as the insertion vector described by Capecchi, M. R., *Science*, 244:1288–92 (1989) which disclosure is hereby incorporated by reference; or a vector based on a promoter trap strategy or a polyadenylation trap, or "tag-and-exchange" strategy described by Bradley, et al., *Biotechnology*, 10:543–539 (1992); and Askew, et al., *Mol. Cell. Biol.*, 13:4115–5124 (1993) which disclosures are also incorporated herein by reference.

One of skill in the art will readily recognize that a large number of appropriate vectors known in the art can be used as the basis of a suitable targeting vector. In practice, any vector that is capable of accommodating the recombinant nucleic acid sequence required to direct homologous recombination and to disrupt the target gene can be used. For example, pBR322, pACY164, pKK223-3, pUC8, pKG, pUC19, pLG339, pR290, pKC101 or other plasmid vectors can be used. Alternatively, a viral vector such as the lambda gt11 vector system can provide the backbone (e.g. cassette) for the targeting construct.

According to techniques well known to those of skill in the art genetically engineered (e.g., transfected using electroporation or transformed by infection) embryonic stem cells are routinely employed for the production of transgenic non-human embryos. Embryonic stem (ES) cells are pluripotent cells isolated from the inner cell mass of mammalian blastocyst. ES cells can be cultured in vitro under appropriate culture conditions in an undifferentiated state and retain the ability to resume normal in vivo development as a result of being combined with blastocyst and introduced into the uterus of a pseudopregnant foster mother. Those of skill in the art will recognize that various stem cells are known in the art, for example AB-1, HM-1, D3. CC1.2, E-14T62a, RW4 or JI (Teratomacarcinoma and Embryonic Stem Cells: A Practical Approach, E. J. Roberston, ed., IRL Press).

It is to be understood that the UCP2 knockout mammals described herein can be produced by methods other than the embryonic stem cell method described above, for example by the pronuclear injection of recombinant genes into the pronuclei of one-cell embryos or other gene targeting methods which do not rely on the use of a transfected ES cell, and that the exemplification of the single method outlined above is not intended to limit the scope of the invention to animals produced solely by this protocol.

The transgenic UCP2 knockout mammals described herein can also be bred (e.g., inbred, outbred or crossbred) with appropriate mates to produce colonies of animals whose genomes comprise at least one non-functional allele of the endogenous gene which naturally encodes and expresses functional UCP2. Examples of such breeding strategies include but are not limited to: crossing of heterozygous knockout animals to produce homozygous animals; outbreeding of founder animals (e.g., heterozygous or homozygous knockouts) with a mouse whose inbred genetic background confers aberrant insulin and/or glucose homeostasis or which provide an animal model of diabetes and crossbreeding a founder animal with an independent transgenic animal which has been genetically engineered to overexpress a gene associated with increased susceptibility to diabetes and/or obesity. For example, a founder knockout mouse could be bred with the ob/ob mouse, the db/db mouse and/or the AY mouse.

In an alternative embodiment of the instant invention transgenic embryonic stem cells can be engineered to comprise a genome which comprises disruptions of more than one gene whose polypeptide product has been implicated in insulin secretion and/or energy homeostasis. For example, an embryonic stem cell can be genetically-engineered via homologous recombination to comprise disruptions which effect both the UCP2 and UCP3 genes. In one embodiment, a targeting construct comprises a first nucleotide sequence comprising genomic UCP3 sequence upstream of (e.g., 5' of) an expression cassette and a second nucleotide sequence comprising genomic UCP2 sequence located downstream (e.g., 3' of) the expression cassette. Such a targeting construct can be introduced into ES cells which produce a transgenic ES comprising a disruption of the UCP2 and UCP3 genes. The resulting transgenic double knockout embryonic stem cell can be used in the techniques described herein and known to those of skill in the art to produce a UCP2/UCP3 double knockout transgenic mammal (founder mammal). The resulting UCP2/UCP3 double knockout transgenic founder can be mated to generate UCP2/UCP3 double knockout mammal comprising heterozygous or homozygous disruptions of UCP2 and/or UCP3. It is also noted that UCP2/UCP3 double knockout mammal can be produced by generating separate lines of mammals whose genome comprise homozygous disruptions in their endogenous UCP2 and UCP3 and crossbreeding these two knockout mammals to produce a double knockout mammal.

The UCP2 knockout mammals, cell lines, primary tissue or cell cultures, cellular extracts or cell organelles (e.g., mitochondria) isolated from the UCP2 knockout mammals of the instant invention are useful for a variety of purposes. In one embodiment of the present invention the transgenic UCP2 knockout mammals produced in accordance with the present invention are utilized as a source of cells for the establishment of cultures or cell lines (e.g., primary, immortalized) useful as indicator cells for the elucidation of the roles in UCP2 in cellular function. As used herein the term indicator cell refers to a cell which performs a UCP2-regulated cellular function which relies on the generation of ATP such as oxidative phosphorylation or insulin release. The term encompasses indicator cells which originate in nature, for example cells isolated from mammalian tissues (e.g., pancreatic β-cells) and cells which have genetically engineered to perform a particular function, for example insulin secretion. The indicator cells isolated or produced from the tissues of a knockout animal of the instant invention would be expected to have the same genotype as the donor animal from which they are derived. The primary cell cultures, or cell lines, can be derived from any desired tissue or cell-type which normally express high levels of UCP2 mRNA, including but not limited to heart, kidney, spleen, white adipose tissue and pancreatic islets.

For example, it is desirable to produce panels of cell lines which differ in their expression of one of more genes. Thus, the present invention encompasses a cell line in which an endogenous UCP2 gene has been disrupted (e.g., UCP2 knockout cells or cell lines such as a pancreatic β- cell or -cell line). The resulting UCP2-functionally disrupted cell comprises a genotype which differs from its parental wild-type cell in a defined manner and thereby allows for the elucidation of the effects of UCP2-deficiency on glucose-stimulated insulin production, ADP or ATP levels or the ratio of ATP/ADP. In another embodiment, a UCP2 knockout cell or cell line can be engineered using skills known in the art. For example, cells which do not possess an endogenous UCP2 gene or which normally do not express UCP2 can be engineered to do so. For example, an exogenous UCP2 gene can be introduced into a cell which does not possess an endogenous UCP2 gene wherein the cell expresses UCP2 due to the presence of the exogenous UCP2 gene. Alternatively, exogenous nucleic acid can be spliced into the genome of a cell which does not normally express UCP2 in order to "turn on" the normally silent UCP2 gene. The agent can be for example, a nucleic acid molecule, a polypeptide, an organic molecule, an inorganic molecule, a fusion protein etc. silent, endogenous UCP2 gene. Subsequently the UCP2 gene in the engineered cells can be disrupted using the methods described herein and known to those of skill in the art for use in the methods and compositions of the present invention.

The availability of UCP2 knockout cells and mammals (e.g., homozygous, heterologous) facilitate the genetic dissection of UCP2-mediated signaling pathways and allow for the identification of UCP2 specific inhibitors. For example, an agent which inhibits the uncoupling function of UCP2 equally in a knockout cell line and its wild-type parental cell line would be recognized as a non-UCP2-specific inhibitor, while an agent which inhibits a UCP2-dependent function in a wild-type which has no effect in the knockout cell line would be recognized as a UCP2 specific inhibitor. Further, the use of cell lines which have disruptions in more than one uncoupling protein (UCP) gene, for example a cell line in which UCP1 and UCP3 or UCP2 and UCP3 have been disrupted could facilitate the identification of agents with potential therapeutic value for the treatment of diseases in which altered UCP function plays a role.

Other embodiments of the invention provide in vitro and in vivo methods of identifying an agent that inhibits the activity (function) of mammalian UCP2 (e.g., an antagonist, a partial antagonist). An inhibitor of UCP2 includes any agent that inhibits UCP2 gene expression (partial or complete) or function (partial or complete) of the UCP2 protein. According to the instant invention, the agent can be combined with a cell, a primary tissue (e.g., pancreatic islet cells), and/or administered to a whole animal. As demonstrated in the following examples, administration can be accomplished in various ways such as the addition to culture media, tissue perfusion, by expressing it from a vector, or by injection.

In one embodiment, a suitable in vitro screening method comprises combining cells which comprise a wild type UCP2 gene (wild type cells), an amount of glucose sufficient to stimulate insulin production and the agent; and combining cells which lack a functional UCP2 gene (UCP2 knockout cells), an amount of glucose sufficient to stimulate insulin production of the cells and the agent. The cells are maintained under conditions appropriate to stimulate insulin production. The amount of insulin produced by the wild type cells is compared to the amount of insulin produced by the UCP2 knockout cells, wherein if the amount of insulin produced by the wild type cells is increased compared to the amount of insulin produced by the knockout cells, then the agent inhibits UCP2.

The in vitro screening method can further comprise the use of any suitable control. For example, in one embodiment, the in vitro screening method can further comprise combining the wild type cells with an amount of glucose sufficient to stimulate insulin production in the absence of the agent; and combining UCP2 knockout cells with an amount of glucose sufficient to stimulate insulin production in the absence of the agent. The cells are maintained under conditions appropriate to stimulate insulin production. The amount of insulin produced by the wild type cells in the presence of the agent is compared to the amount of insulin produced by the wild type cells in the absence of the agent; and the amount of insulin produced by the UCP2 knockout cells in the presence of the agent is compared to the amount of insulin produced by the UCP2 knockout cells in the absence of the agent. If the amount of insulin produced by the wild type cells in the presence of the agent is increased compared to the amount of insulin produced by the wild type cells in the absence of the agent, and the amount of insulin produced by the UCP2 knockout cells in the presence of the agent is similar to the level produced by the knockout cells in the absence of the agent, then the agent inhibits UCP2. According to the instant invention, an appropriate pancreatic β-cell based assay for the identification of agents which inhibit UCP2-mediated regulation of insulin secretion can be practiced with cells characterized by a disruption of the UCP2 gene selected from the group consisting of: a homozygous disruption and a heterozygous disruption.

Another embodiment of the present invention provides an in vivo screening method for determining whether an agent inhibits UCP2. The increased glucose-sensitivity of the transgenic non-human UCP2 knockout mammals of the instant invention can be utilized as the basis of a screening assay in which an agent that is being evaluated for its ability to inhibit the UCP2-mediated negative regulation of insulin production in response to glucose stimulation. In one embodiment, a suitable in vivo screening method comprises administering to a non-human mammal which comprise a wild type UCP2 gene (wild type mammal), an amount of glucose sufficient to stimulate insulin production and the agent; and combining a transgenic non-human mammal which lacks a functional UCP2 gene (UCP2 knockout mammal), an amount of glucose sufficient to stimulate insulin production of the cells and the agent. The amount of insulin produced by the mammals is measured. The amount of insulin produced by the wild type mammal compared to the amount of insulin produced by the UCP2 knockout mammal, wherein if the amount of insulin produced by the wild type mammal is increased compared to the amount of insulin produced by the knockout mammal, then the agent inhibits UCP2.

The in vitro screening method can further comprise the use of any suitable control. For example, in one embodiment, the in vitro screening method can further comprise administering to a wild type mammal an amount of glucose sufficient to stimulate insulin production in the absence of the agent; and administering to a UCP2 knockout mammal an amount of glucose sufficient to stimulate insulin production in the absence of the agent. The amount of insulin produced by the mammals is measured. The amount of insulin produced by the wild type mammal in the presence of the agent is compared to the amount of insulin produced by the wild type mammal in the absence of the agent; and the amount of insulin produced by the UCP2 knockout mammal in the presence of the agent is compared to the amount of insulin produced by the UCP2 knockout mammal in the absence of the agent. If the amount of insulin produced by the wild type mammal in the presence of the agent is increased compared to the amount of insulin produced by the wild type mammal in the absence of the agent, and the amount of insulin produced by the UCP2 knockout mammal in the presence of the agent is similar to the level produced by the knockout mammal in the absence of the agent, then the agent inhibits UCP2.

In the in vitro and in vivo screening methods of the present invention, the amount of insulin produced by the cells or the transgenic UCP2 knockout mammal can be determined using a variety of methods as described herein or known to those of skill in the art.

An alternative embodiment of the invention provides a method of identifying a UCP2 mimic (e.g., a recombinant peptide, polypeptide or fusion protein) which is capable of restoring one or more UCP2-dependent functions (e.g, negative regulation or uncoupling activity) to a cell (or entire organism, for example an individual) which is characterized by a lack of UCP2 function. According to this embodiment of the invention the transgenic UCP2 knockout mammals or their cells, tissues, cellular extracts or organelles provide a starting material, or control material, in which the function of potential UCP2 mimics can be evaluated. Also encompassed by the present invention is an method of identifying an agent which mimics UCP2 activity. In one embodiment, the method comprises introducing the agent into cells which lack a functional UCP2 gene and determining whether a UCP2-mediated cellular function (one or more) occurs in the presence of the agent. If UCP2-mediated cellular function occurs in the cells which lack a functional UCP2 gene in the presence of the agent, then the agent is a UCP2 mimic.

In another embodiment, the method of identifying an agent which mimics UCP2 activity comprises introducing the agent into a transgenic non-human mammal which lacks a functional UCP2 gene and determining whether a UCP2-mediated cellular function (one or more) occurs in the presence of the agent. If UCP2-mediated cellular function occurs in the transgenic non-human mammal which lacks a functional UCP2 gene in the presence of the agent, then the agent is a UCP2 mimic.

In the method of identifying a UCP2 mimic, a UCP2-mediated cellular function includes, for example, altered insulin/glucose homeostasis and responsiveness to glucose stimulation, altered mitochondrial activity, decreased responsiveness to glucose-stimulation, decreased level of insulin production, decreased ambient fed-state serum insulin levels combined with a decreased glucose level, compared to that of the UCP2 knockout cell or mammal.

One of skill in the art will know of appropriate techniques for the introduction and/or expression of potential mimics. For example, a library of nucleotide sequences (e.g., cDNA sequences) encoding potential mimics could be introduced (e.g., transfected or transduced in the context of an expression vector) and expressed in an appropriate host cell isolated from the knockout mammals provided herein, or in a host cell which has been produced via homologous recombination using a UCP2 targeting vector according to the instant invention, and screened for the restoration of a UCP2-dependent cellular function (e.g., decreased membrane potential, uncoupled cellular respiration, altered ATP/ADP ratio, increased insulin production). For example, a potential UCP2 mimic includes recombinant nucleic acid sequences which encode a truncated UCP2 polypeptide in combination with a nucleic acid comprising a coding sequence derived from another protein (e.g. a fusion protein), for example nucleic acid sequence which encodes a domain of another uncoupling protein, or nucleic acid sequence which provides for examples an inducible promoter sequence or which introduces a cis-acting regulatory sequence. Thus, potential mimics can include portions of a recombinant or naturally occurring UCP2 polypeptide derived from the same mammalian species or from a different mammalian species.

The present invention also relates to methods of treatment or prevention of conditions (e.g., hyperglycemia) or diseases (e.g., type 2 diabetes) associated with aberrant UCP2 function (e.g., negative regulation or uncoupling activity). For example the invention provides a method of treating (e.g., alleviating the symptoms of) or preventing (e.g., in a individual who is predisposed to develop) altered glucose/insulin homeostasis. In one embodiment the invention provides a method of increasing insulin production in an individual comprising administering to the individual an agent which inhibits UCP2 activity. In a second embodiment the invention provides a method of decreasing blood glucose in an individual comprising administering to the individual an agent which inhibits UCP2 activity. The invention further provides a method of treating diabetes (e.g., type 2 diabetes) in an individual comprising administering to the individual an agent which inhibits UCP2 activity. The invention also provides methods of modulating mammalian mitochondrial activity (e.g., respiration rates and inner mitochondrial membrane potential). For example, another embodiment of the invention provides a method of enhancing coupling of mitochondria in an individual comprising administering to the individual an agent which inhibits UCP2 activity. This embodiment can be evidenced as increased ratio of state 3 (presence of ADP)/state 4 (absence of ADP respiration). Alternatively, the invention provides a method of enhancing uncoupling of mitochondria in an individual comprising administering to the individual an agent which enhances (induces) UCP2 activity.

The agent for use in the methods of the present invention can be for example, a nucleic acid molecule (e.g., DNA, RNA, antisense DNA, antisense RNA), a protein, a peptide, a polypeptide, a glycoprotein, a polysaccharide, an organic molecule, an inorganic molecule, a fusion protein etc.

The agents (e.g., therapeutic agents such as UCP2 inhibitors or UCP2 mimics) can be administered to a host in a variety of ways. Potential routes of administration include intradermal, transdermal (e.g., utilizing slow release polymers), intramuscular, intraperitoneal, intravenous, subcutaneous or oral routes. Any convenient route of administration can be used, for example, infusion or bolus injection, or absorption through epithelial or mucocutaneous linings.

The agent can be administered in combination with other components such as pharmaceutically acceptable excipients, carriers, vehicles or diluents.

In the treatment methods designed to inhibit the function of UCP2, an "effective amount" of the agent is administered to an individual. As used herein the term "effective amount" an amount that inhibits (or reduces) the activity of UCP2, and results in a significant (e.g., a statistically significant) difference (e.g., increase, decrease) in a cellular function which is normally subject to regulation (e.g., negative regulation) by UCP2. For example, an effective amount of a therapeutic agent administered to an individual who is hyperglycemic would comprise an amount sufficient to alter (inhibit) UCP2-mediated negative-regulation of insulin production which thereby facilitates the production and release of more insulin. The amount of agent required to inhibit UCP2 activity will vary depending on a variety of factors including the size, age, body weight, general health, sex and diet of the host as well as the time of administration, and the duration or stage of the particular condition or disease which is being treated. Effective dose ranges can be extrapolated from dose-response curves derived in vitro or an in vivo test system which utilizes the transgenic non-human UCP2 mammals described herein.

The following examples are offered for the purpose of illustrating the present invention and are not to be construed to limit the scope of this invention.

EXAMPLE 1

Production of UCP2 Knockout Mouse

In order to assess the physiologic function of UCP2, UCP2-deficient transgenic non-human mammal which lacks a functional UCP2 gene were produced. Homozygous (−/−) animals lack an intact UCP2 gene and fail to express intact UCP2 mRNA in all tissues tested, including heart, kidney, spleen, white adipose tissue and pancreatic islets which normally express high levels of UCP2 mRNA. Of note, UCP2 mRNA was also observed to be reduced in pancreatic islets isolated from heterozygous (+/−) animals.

Mapping Murine UCP2 Genomic Clones: Two UCP2 genomic clones were obtained after screening a P1 c129/SVJ genomic library (Genome Systems Inc., St. Louis, Mo.). Both clones were mapped using Southern blot analysis and end labeled oligonucleotide probes designed according to mouse UCP2 cDNA sequence.

Targeting Construct: A replacement targeting construct was prepared in which a segment of the UCP2 gene between introns 2 and 7 including the start codon was removed and replaced with a PGK-NEO-Poly(A) expression cassette. (C. N. Adra et al. Gene 60, 65 (1987)). More specifically, the targeting vector was constructed which contains approximately 8.7 kb of homologous mUCP2 genomic DNA, with 5.5 kb located 5' and 3.2 kb located 3' of the PGK-NEO-Poly(A) cassette. The PGK-NEO-Poly(A) cassette replaces approximately 2 kb of mUCP2 genomic sequence between restriction sites Xho 1(intron 2) and Sph I (intron 7). The Southern blot probe is located outside the targeting vector sequence. To detect targeted clones, genomic DNA was digested with SacI.

FIG. 2 shows a partial restriction enzyme map of the mUCP2 gene, the UCP2 KO targeting vector and the predicted structure of the recombinant allele. The empirically determined map is consistent with a previously reported genomic map (Gimeno, R. E., et al., *Diabetes*, 46(5):900–906 (1977); Fleury, C. and Sanchis, D., *Int. J. Biochem. Cell Biol.*, 31(10): 1261–1278 (1999). In FIG. 2, the filled boxes refer to exons corresponding to coding sequence, the locations of which have been previously published, and the arrow refers to the orientation of transcription of the PGK-NEO cassette.

Gene Targeting by Homologous Recombination: The targeting plasmid was linearized with Sac I and electroporated in J1 embryonic stem cells (E. Li, et al., *Proc. Natl. Acad. Sci. U.S.A.*, 90:1590 (193) (provided by E. Li, A Sharp and R. Jaenisch). Gene targeting was performed as previously described (Shimada, M., et al., *Nature* 396:,670 (1998); Adra, C. N., et al., *Gene*, 60:65 (1987); Li, E., et al., *Proc. Natl. Acad. Sci. USA*, 90:1590 (1993); Ramarez-Solos, R., *Gene Targeting and Embryonic Stem Cells, Meth. Enzymol.*, 225:855–878 (1993); *Manipulating the Mouse Embryo, A Laboratory Manual, Second Edition*, Cold Spring Harbor Laboratory Press (1994)). Selection with G418 (neomycin) resulted in the isolation and a expansion of five positive clones followed by genomic DNA extraction for Southern blot analysis. Five positive clones were injected into C57B1/6 embryos at the blastocyst stage. Chimeric offspring were mated with C57B1/6 mice. Germline transmission of the mutant allele was determined by PCR of tail genomic DNA. The arrows in FIG. 2 (middle panel) refer to PCR primers used to genotype (e.g., wild-type, heterozygous or knockout) the mice.

Genotyping: Genotyping was performed by multiplex PCR. Specific primers used to detect the KO allele were sense, 5'cctccactcatgatctatagatc 3' (SEQ ID NO: 1), located in the neo cassette, and antisense, 5' acccctctgtcgccaccatagtca 3' (SEQ ID NO: 2), located in the UCP2 coding sequence. The "knockout allele" primers amplified a 300 bp PCR product. Primers used to detect the wild type allele were sense, 5' gcactgcggcctgttttg 3' (SEQ ID NO: 3), and the same antisense primer described above. The "wild-type allele" primers amplified a 600 bp PCR product.

Standard protocols, well known to those of skill in the art were used for PCR.

Southern and Northern Blot Analysis: One line of mice carrying the disrupted UCP2 was generated (genotype) and characterized for its phenotype according to the methods presented herein. UCP2 mRNA levels (e.g. genotype) were determined by Southern blot analysis on 15 ug of heart, spleen, kidney and white adipose tissue (WAT) total RNA. A full length rat cDNA UCP2 including the whole coding sequence was used as probe. Individual tissues or pooled islets isolated from 6 mice of each genotype were used for RNA extraction. A Northern blot analysis was performed using a full length rat UCP2 cDNA hybridization probe. Standard protocols were used for isolation of RNA and Northern blot. A full length rat cDNA UCP2 including the whole coding sequence was used as probe. Isotopic bands were visualized by autoradiography. Results: Southern blot analysis demonstrates homozygous (−/−) mice lack an intact UCP2 gene and the Northern analysis indicates that the (−/−) knockout mice fail to express intact mRNA in all tissues tested including heart, kidney, spleen, white adipose tissue (WAT) and pancreatic islet cells, all of which normally express high levels of UCP2. The Northern analysis also indicated that UCP2 mRNA is reduced in pancreatic islets from heterozygotes (+/−) mice.

Animal Care: Animals were housed four per care in a temperature controlled room with 12 hr light/dark cycle. Food and water were available ad libitum unless noted. All experiments were conducted in accord with the National Institutes of Health (NIH) Guide for the Care and Use of Laboratory Animals.

EXAMPLE 2

Effect of UCP2 Deficiency on Mitochondrial Respiration

Fuel metabolism generates a mitochondrial proton motive force used by ATP synthase to generate ATP. UCP2 catalyzes a mitochondrial inner membrane proton leak that bypasses ATP synthase, thus providing a potentially important means of decreasing ATP production and hence fuel efficiency. This is schematically illustrated in FIG. 1A which demonstrates that mitochondrial oxidation of fuels generates NADH and $FADH_2$ which donate electrons to the mitochondrial inner membrane electron transport chain. As electrons move down this chain, protons are pumped out of the mitochondrial matrix by complexes I (NADH-ubiquinone oxidoreductase), III (ubiquinone-cytochrome-c oxidoreductase) and IV (cytochrome oxidase), creating a proton electrochemical gradient. Molecular oxygen ($O_2$) is the terminal electron acceptor. Protons are pumped out by complexes I, III and IV of the electron transport chain creating a proton electrochemical gradient ($\Delta\mu_{H+}$). Protons may reenter the mitochondrial matrix via ATP synthase ($F_0F_1$), with energy being used to generate ATP from ADP and Pi. This proton motive force is then used by ATP synthase to generate ATP from ADP (Scheffler, I. E., *Mitochondria (Wiley-Liss, New York*, 1999) pp.141–245.) Alternatively, protons may also reenter via an uncoupling protein (UCP1 or UCP2), with energy being released in the form of heat.

In order to assess the effects of UCP2-deficiency on mitochondrial proton leak, mitochondria were isolated from heart, a site of abundant UCP2 expression, and liver, a site of extremely low UCP2 expression. Respiration was studied in the presence (state 3) or absence of ADP (state 4). When ADP is available (state 3), protons enter via ATP synthase, lowering the proton motive force, decreasing back pressure on electron transport chain proton pumps, thus stimulating respiration (shown schematically in FIG. 1B). As shown below, the ratio of state 3/state 4 respiration (an index of the degree of coupling of respiration to ADP availability) was markedly increased in UCP2 deficient heart mitochondria (See FIG. 3C). This demonstrates that UCP2-deficient mitochondria are more coupled, establishing for the first time that endogenous levels of UCP2 contribute to uncoupling of mammalian mitochondria.

Mitochondria isolation. Mitochondria were isolated from heart of wild type (n=7) and UCP2 KO mice (n=7). Tissue was ground and homogenized in 10–20 ml cold buffer (250 mM sucrose, 10 mM hepes, 0.5 mM EDTA, pH 7.2 with KOH, 0.% BSA) and kept on ice. Homogenate was centrifuged at 600 g for 5 min. The pellet was discarded and the supernatant was centrifuged at 8000 g for 10 min. The mitochondrial pellet was washed twice and finally resuspended in buffer without BSA. The mitochondria were then used for polarography.

Polarography. Mitochondrial respiration was measured in a Clarke type oxygen electrode at 37° C. using the following incubation conditions: 280 mM sucrose, 10 mM tris/maleate pH 6.8, 2.5 mM $KH_2PO_4$, 0.5 mM EDTA, 5 mM succinate and approximately 0.5 mg mitochondrial protein/ml. Data were channeled into an A/D converter and recorded on a Pentium based PC using the DataShuttle A/D converter and the Quicklog Software package. The oxygen electrode was calibrated with experimental buffer saturated with room air assuming a solubility coefficient of 199 nmol 02/ml at 37° C. The uncoupling activity of mitochondria was determined by assessing the ability of added ADP to increase oxygen consumption. (evaluated as a decrease in the ratio between state 3/state 4 of respiration). More specifically, mitochondrial respiration in heart and liver mitochondria was assessed in the presence (state 3) and absence (state 4) of ADP (**23). Respiratory control ratio (state 3/state 4 ratio) is also shown. Results are expressed as mean+/−SE (n=7).

Figures 3A, 3B, 3C:
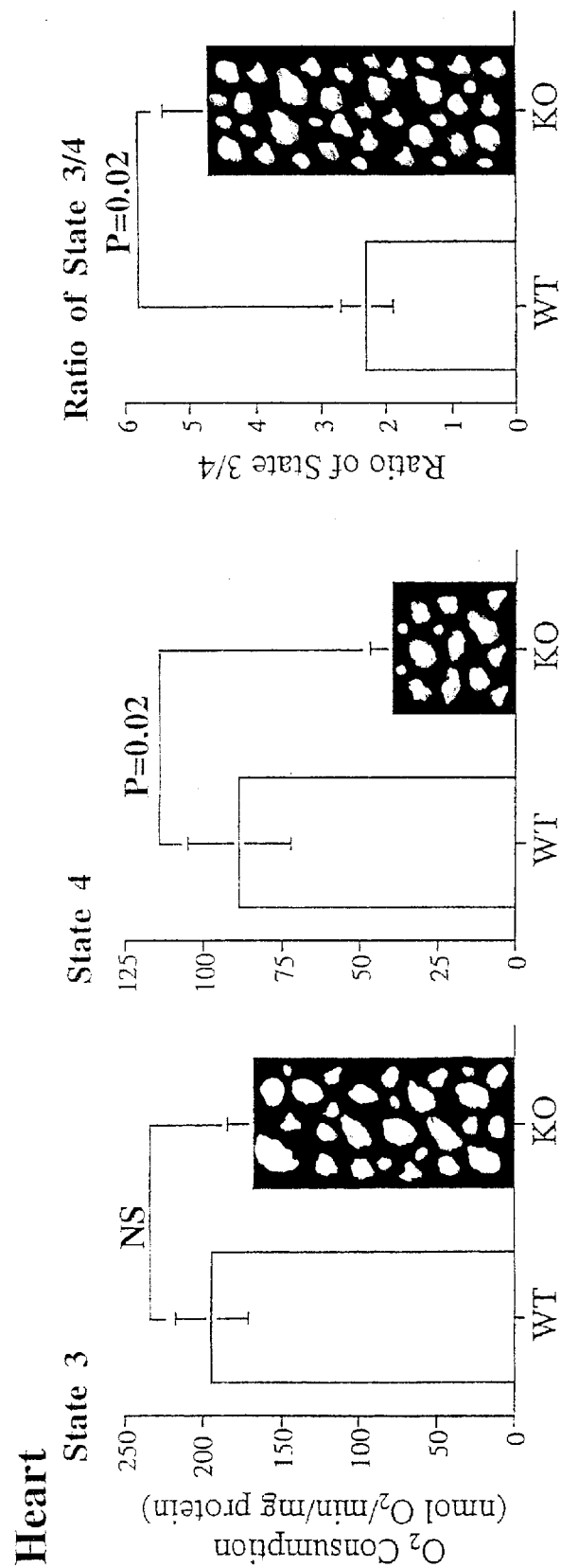
FIGS. 3A–3F are graphic representations demonstrating the effect of UCP2-deficiency on mitochondrial respiration; results are expressed as mean +/–SE (n=7).
Figures 3D, 3E, 3F:
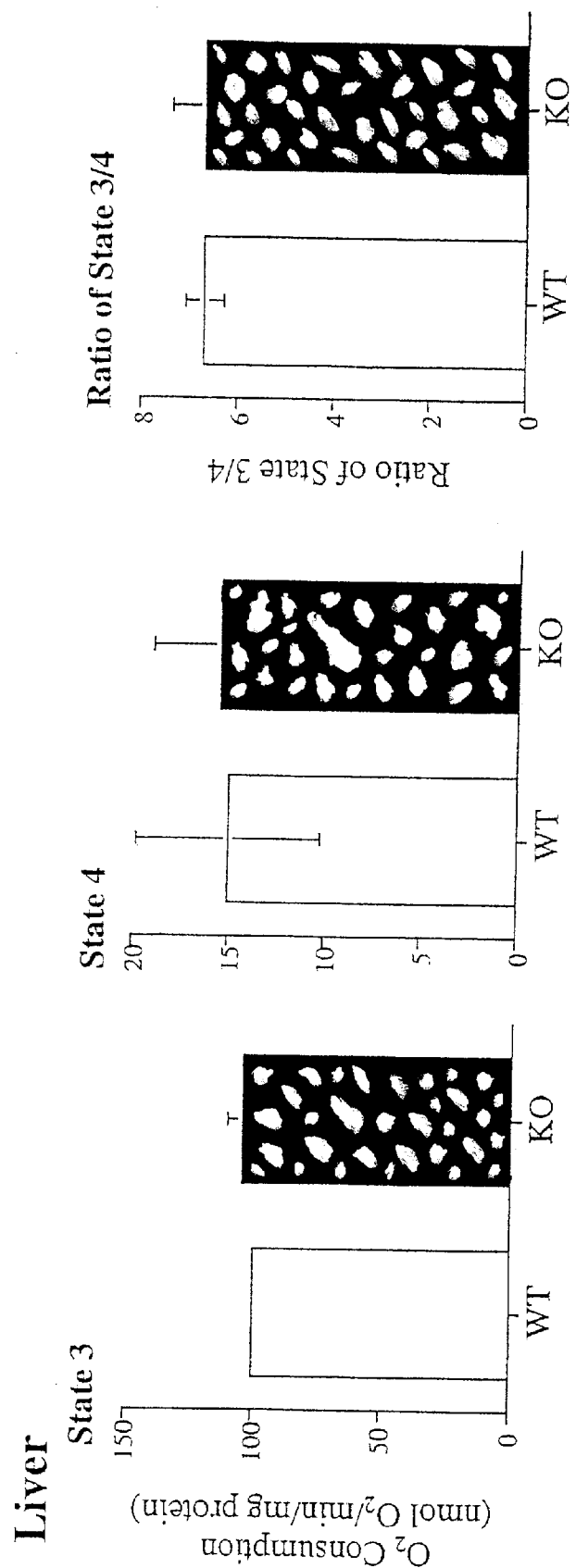

Results: The knockout phenotype (e.g. UCP2 deficiency) was without effect on state 3 respiration of heart mitochondria (FIG. 3A). When ADP is absent (state 4), protons can only enter via a proton leak pathway, such as the one catalyzed by UCP2. Thus in state 4 conditions, respiration is dependent upon the existence of proton leaks. State 4 respiration was markedly reduced (e.g., by 50%) in heart mitochondria isolated from UCP2 knockout mice (FIG. 3B) and the ratio state 3/state 4 respiration was increased 2 fold (FIG. 3C). This result indicates that mitochondria lacking UCP2 are more coupled or have a decreased proton leak relative to the mitochondria which express wild type UCP2. This effect was not seen in liver mitochondria, which express little or no UCP2 (FIGS. 3D–3F). These results establish for the first time that endogenous levels of UCP2 contribute to the uncoupling of mammalian mitochondria.

Statistical analysis: Statistical analysis was performed using StatView 4.0 (Abacus Concept, Berkeley, Calif., USA). Results are presented as the mean+/−SE. Statistical significance was determined using either Unpaired Student t test and ANOVA analysis.

EXAMPLE 3

Effect of UCP2 Deficiency on Thermogenesis and Body Weight Regulation

Given the role of the brown fat-specific UCP1 in regulating cold-induced thermogenesis (Enerback, S., et al, Nature, 387:90 (1997)) and whole body energy balance, it has been postulated that UCP2 might play a similar role. To assess the effect of UCP2-deficiency on thermogenesis and body weights, whole body oxygen consumption and body temperature during cold exposure (4° C.) were assessed in control (+/+) and UCP2-deficient (−/−) mice. Animals were housed four per cage in a temperature controlled room (23° C.) with a 12 hr light/dark cycle and had ad libitum access to chow and water.

Results: No effect on body weight on a chow diet, whole body thermogenesis or thermoregulation was noted. Body weights, whole body oxygen consumption and body temperature during cold exposure were similar in control and UCP2-deficient mice. These results suggest either that UCP2 does not regulate these processes under the conditions studied or that alternative mechanisms compensated for the absence of UCP2. Of note, no upregulation of UCP3 mRNA in heart, muscle or white fat, or UCP1 mRNA in brown fat was observed in UCP2-deficient mice. These results demonstrate that UCP2 is not required for cold exposure-induced thermogenesis or body weight regulation when mice are fed a chow diet.

EXAMPLE 4

Effect of UCP2 Deficiency on Insulin/Glucose Homeostasis

In order to assess the effects of UCP2-deficiency on ambient (e.g., resting) insulin/glucose homeostasis blood was obtained from fed and fasted wild-type (WT, +/+), heterozygous (HT, +/−) and knockout (KO, −/−) littermates for resting blood glucose and insulin determinations.

Serum insulin and blood glucose determinations: Blood was obtained from fed and overnight fasted animals between 8 am and noon. Glucose was assessed using a glucometer (One touch, Lifescan, Milpitas, Calif.) and insulin via an ELISA assay (Crystal Chem Inc., Chicago, Ill.) with rat insulin as a standard.

Figure 4B:
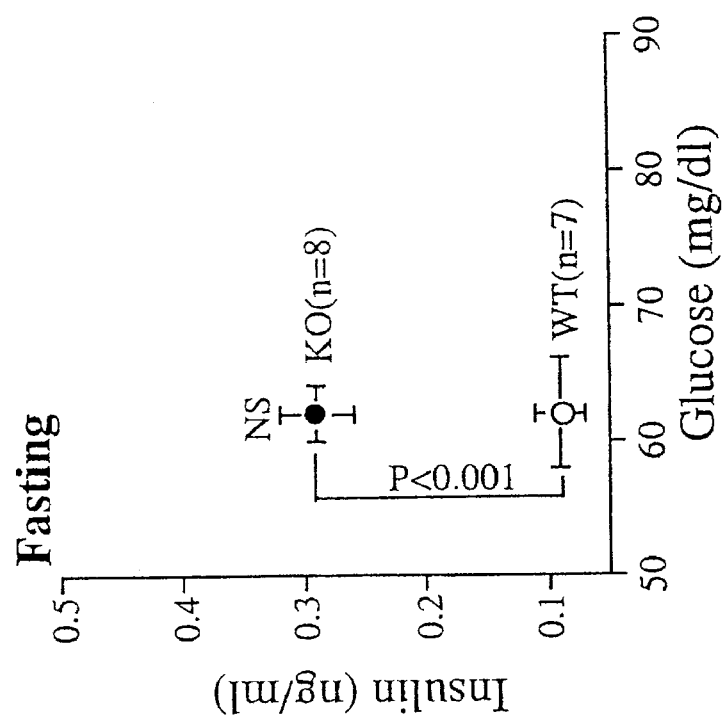
FIGS. 4A and 4B are graphic representations demonstrating ambient serum insulin and blood glucose levels in fed (FIG. 4A) and fasted (FIG. 4B) wild-type (+/+), heterozygous (+/–) and knockout (–/–) mice.
Figure 4A:
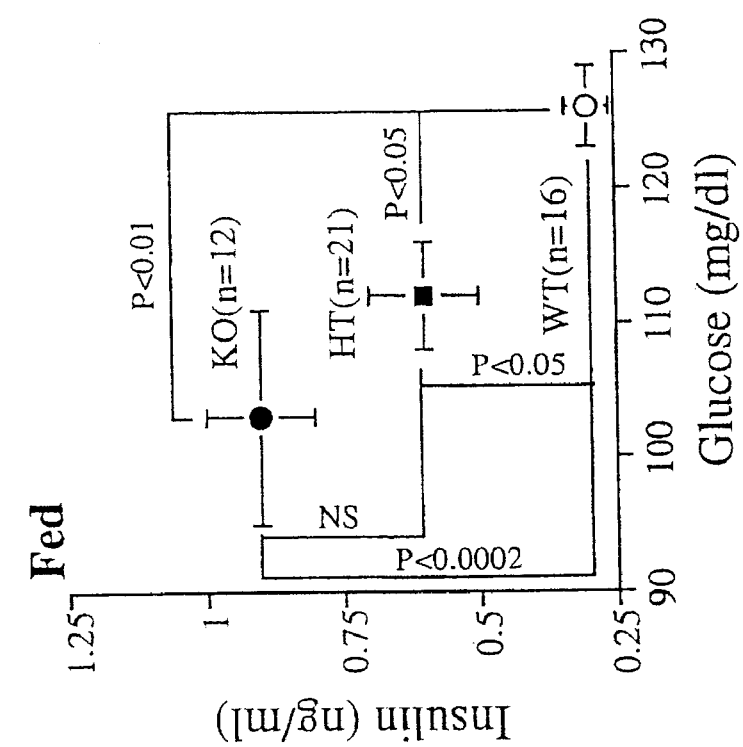
Figure 4D:
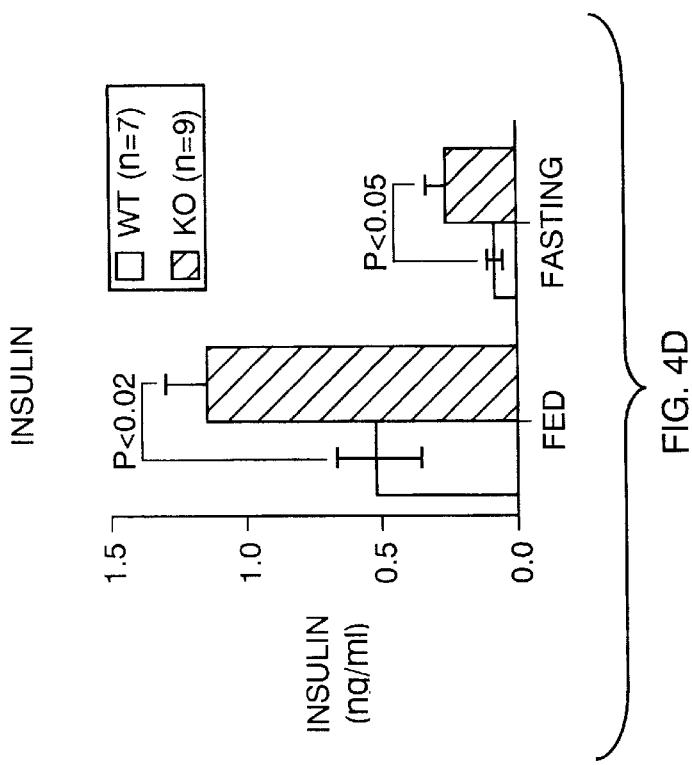
FIGS. 4C and 4D are graphic representations demonstrating blood glucose (FIG. 4C) and insulin levels (FIG. 4D) of fed- and fasted-state wild type (+/+) and UCP2 knockout (–/–) mice. Data are mean+SE.
Figure 4C:
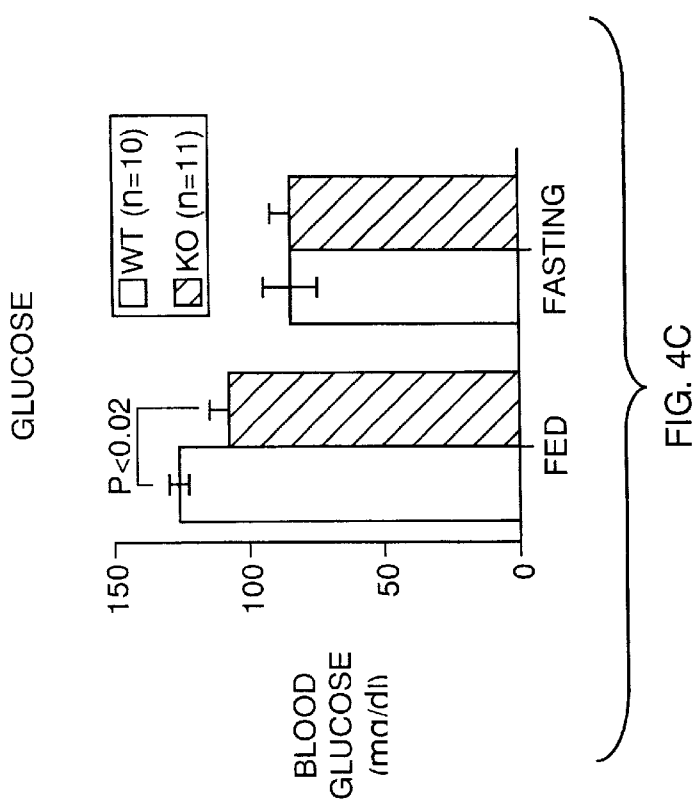

Results: In the fed state, homozygous (−/−) animals had 2.8-fold higher serum insulin and 18% lower blood glucose levels (FIGS. 4A, 4C and 4D). In heterozygous animals (+/−), insulin and glucose levels were intermediate, being elevated by 2.0-fold and decreased by 11%, respectively. Importantly, circulating blood insulin and glucose levels were intermediate in UCP2+/−mice (FIG. 4A). This intermediate effect observed in heterozygotes is consistent with the decreased expression of UCP2 mRNA in islets mentioned earlier and illustrates that relatively small changes in UCP2 activity (i.e., a 50% reduction) have physiologically relevant effects on insulin secretion. This is reminiscent of effects of glucokinase hemizygosity on insulin secretion (Grupe, A., et al., Cell, 83:69 (1995); Bali, D., et al., J. Biol. Chem., 270:21464 (1995); Terauchi, Y., et al., J. Biol Chem., 270:30253 (1995)) and lends support to the theory that UCP2 is an important regulator of insulin secretion.

In the fasted state, blood glucose and insulin levels fell in both control and homozygous animals (FIG. 4B) with glucose values being equal in homozygous and control fasted mice. Insulin levels, however, remained 3-fold higher in homozygous versus control fasted animals.

Statistical analysis: Statistical analysis was performed using StatView 4.0 (Abacus Concept, Berkeley, Calif., USA). Results are presented as the mean+/−SE. Statistical significance was determined using either Unpaired Student t test and ANOVA analysis.

EXAMPLE 5

Effect of UCP2 Deficiency on Glucose Clearance During a Glucose Tolerance Test

In order to assess the effect of UCP2 deficiency on glucose clearance an intraperitoneal (i.p.) glucose tolerance test (IPGTT) was assessed following an overnight fast.

Glucose tolerance test: Wild type (+/+) and UCP2 KO (−/−) mice were injected 1 g/kg glucose after an overnight fast. Blood were collected in 0, 10, 20, 30, 60, 120 min after injection for glucose measurement and in 0, 30, and 120 min after injection for insulin measurement.

Figure 5A:
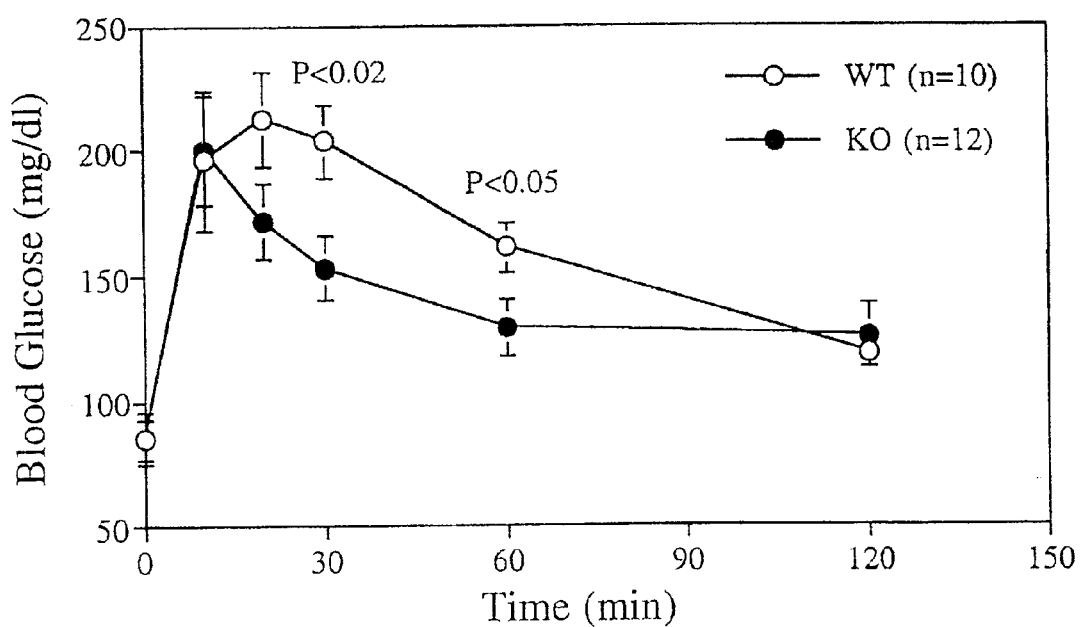
FIG. 5A is a graphic representation demonstrating the blood glucose and insulin levels of wild type (+/+) and knockout (–/–) mice during an intraperitoneal glucose tolerance test (IPGTT).
Figure 5C:
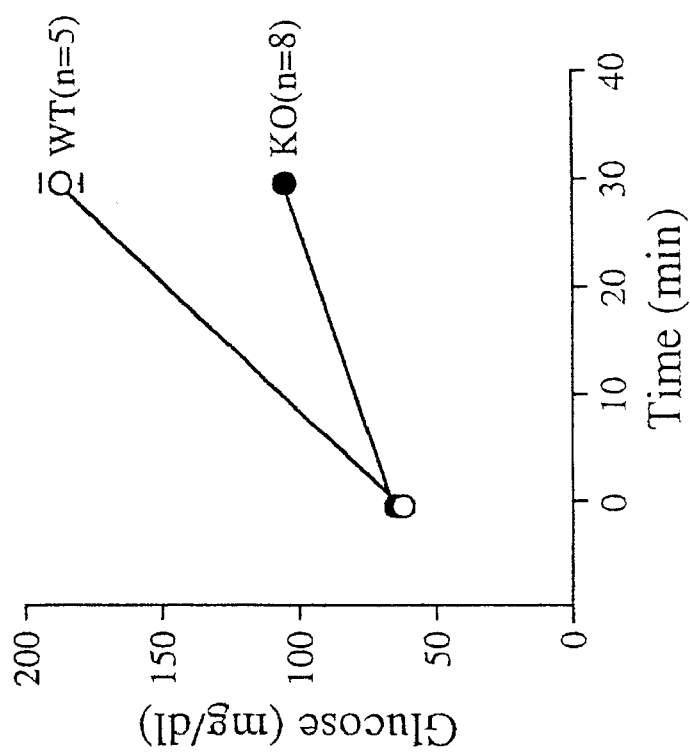
FIGS. 5B and 5C present serum insulin (FIG. 5B) and blood glucose levels (FIG. 5C) before and 30 minutes after the intraperitoneal injection of wild type (+/+) and knockout (–/–) mice with glucose.
Figure 5B:
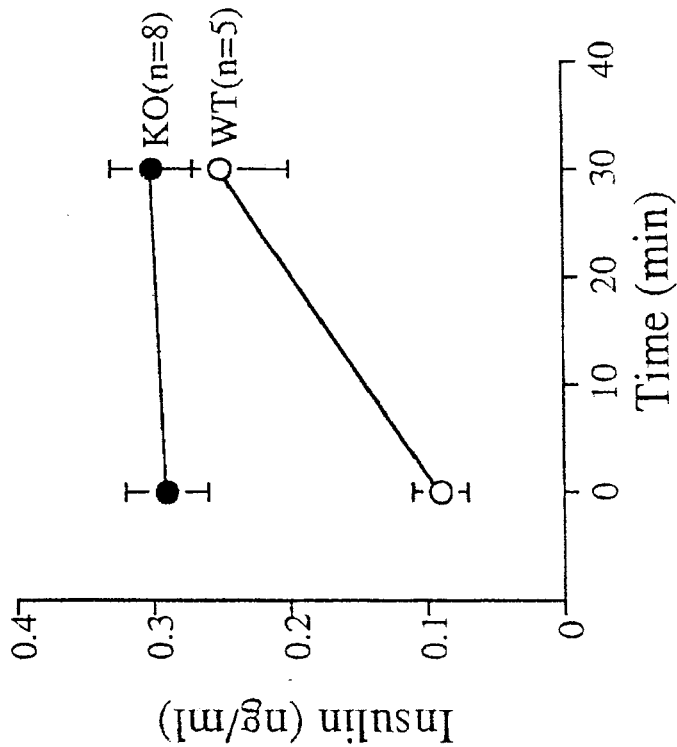

Results: UCP2-deficient animals had markedly increased glucose clearance during the IPGTT (FIG. 5A). In a separate group of animals, serum insulin and glucose levels were checked prior to and 30 minutes following glucose administration. As expected, insulin increased 2.8-fold in control animals 30 minutes following the glucose challenge (FIG. 5B, left panel). As previously noted (FIG. 4A), baseline insulin levels were elevated by 3.2-fold in fasted UCP2-deficient mice. These elevated insulin levels were not increased further 30 minutes into the IPGTT (FIG. 5C, left panel). This is likely to be due to the fact that glucose, in these UCP2-deficient animals, was not markedly increased at 30 minutes (FIG. 5C right panel).

Statistical analysis: Statistical analysis was performed using StatView 4.0 (Abacus Concept, Berkeley, Calif., USA). Results are presented as the mean+/−SE. Statistical significance was determined using either Unpaired Student t test and ANOVA analysis.

EXAMPLE 6

Effect of UCP2 on Glucose-Stimulated Insulin Production

Figure 1B:
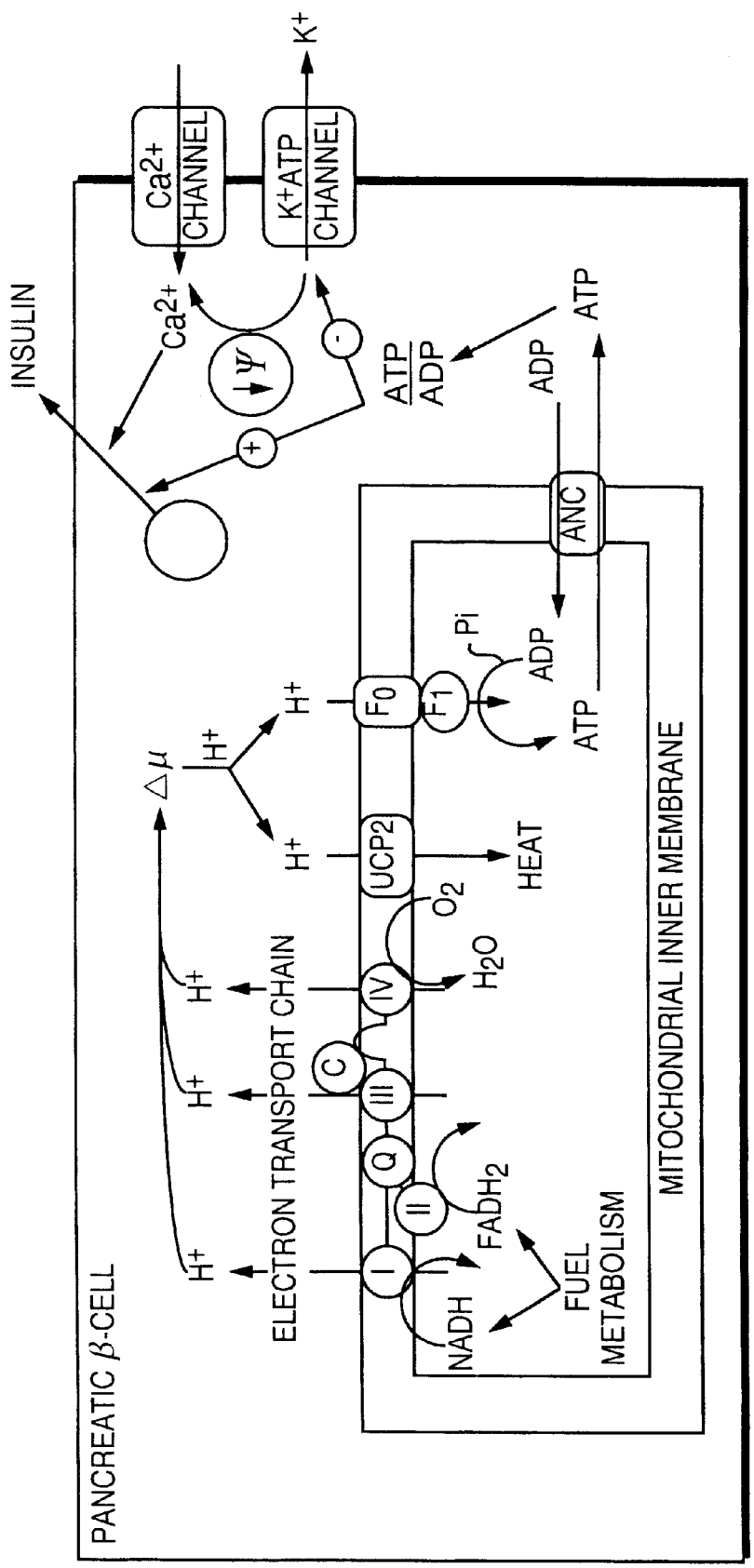
FIG. 1B is a schematic representation of the role played UCP2 in the regulation of insulin secretion by pancreatic β-cells; abbreviations: ANC, adenine nucleotide carrier; C, cytochrome C; Q, ubiquinone.

UCP2 mRNA and protein are normally expressed at high levels in the pancreatic β-cells of mammals whose genomes comprise a wild-type UCP2 gene. FIG. 1B presents a schematic representation which demonstrates that β-cells utilize the ATP/ADP ratio to couple oxidative glucose metabolism to insulin secretion (Ashcroft, F. M., et al., Diabetologia, 42:903 (1999); Matschinsky, F. M., et al., Diabetes, 47:307 (1998); Newgard, C. B., and McGarry, J. D., Annu. Rev. Biochem., 64:689 (1995)). Thus, glucose-stimulated insulin secretion by pancreatic β-cells depends upon mitochondria activity and ATP levels. The increased ATP/ADP ratio promotes insulin secretion via mechanisms independent of altered membrane potential (Gembal, M., et al., J. Clin. Invest., 91:871 (1993); Takahashi, N., et al, Proc. Natl. Acad. Sci. U.S.A., 96:760 (1999)). More specifically, ATP, and/or an increased ATP/ADP ratio, closes the ATP-sensitive potassium $K_{ATP}$ channel in pancreatic β-cells causing plasma membrane depolarization, influx of $Ca^{2+}$, and finally, insulin secretion. The rise in the intracellular calcium concentration in the beta cell ultimately triggers insulin granule exocytosis.

Given the proton leak activity of UCP2 and its predicted negative effect on ATP synthesis, it was proposed that UCP2 might be a negative regulator of insulin secretion (Chan, C. B., et al., Diabetes 48:1482 (1999)). In support of this view, adenoidally-mediated overexpression of UCP2 in isolated pancreatic rat islets caused decreased glucose-stimulated insulin secretion. Using a similar approach, another study overexpressed UCP2 in islets of obese ZDF rats (Wang, M. Y., et al., Diabetes, 48:1020 (1999)). These animals lack normal leptin receptors, develop obesity-induced type 2 diabetes (noninsulin-dependent diabetes (NIDDM)) and have defective glucose-stimulated insulin secretion (Unger, R. H., Diabetes, 44:863 (1995)). In apparent contrast to the study in nonnal rat islets(Chan, C. B., et al., Diabetes 48:1482 (1999)), UCP2 overexpression in ZDF islets improved glucose-stimulated insulin secretion (Wang, M. Y., et al., Diabetes, 48:1020 (1999)). These "gain-of-function" overexpression studies suggest that UCP2 plays a role in regulating insulin secretion, however, the nature of this effect in vivo, and in different physiologic and pathophysiologic situations, is not known. It is also unknown whether endogenous levels of UCP2, as opposed to ectopically overexpressed levels of UCP2, have a similar negative effect on insulin secretion. Elevated blood insulin in the face of decreased blood glucose strongly suggests that the pancreatic β-cells of UCP2-deficient mice have increased responses to glucose and oversecrete insulin.

UCP2 could also negatively regulate insulin secretion in pancreatic β-cells by decreasing ATP production, which couples glucose metabolism to insulin secretion. In pancreatic β-cells, increased ATP or ATP/ADP ratio inhibits the $K^+_{ATP}$ channel, decreasing plasma membrane potential (Ψ), leading to an influx of $Ca^{2+}$ and secretion of insulin (FIG. 1B). In order to evaluate the effects of UCP2-deficiency on glucose-stimulated insulin production pancreatic insulin secretion, isolated pancreatic perfusion and isolated islet studies were performed on control (+/+) and homozygous (−/−) littermates.

Pancreatic Perfusion: Control (wild type +/+) or knockout (−/−) mice were fasted overnight (15–18 hours) and then anesthetized with 80 mg/kg ip sodium pentobarbital. The surgical procedure for the perfusion of the pancreas was similar to that described in Pederson, R. A., et. al., Diabetes, 47:1046 (1998). In brief, PE 10 tubing (Intramnedic, Parsippany, N.J.) was used to cannulate the aorta and portal vein. The pancreas was perfused through the aorta with a Krebs-Ringer-2% BSA-Glucose-3% Dextran (KRBGD) solution and fractions were collected at 1 minute intervals from the portal vein. The KRBGD solution was gassed with 95% $O_2$/5% $CO_2$ to achieve a pH of 7.4 and the concentration of glucose was either 1.4 mM (low glucose) or 20 mM (high glucose). The infusion pump was a Gilson Minipuls 2 (France).

Isolation of Pancreatic Islets: Mice were anesthetized with 60 mg/kg sodium pentobarbital i.p. Pancreatic islets were isolated according to the method of Cawthorn and Chan, except that the total exposure to type XI collagen (Sigma, St. Louis, Mo.) was 30 min and the dextran gradient was altered to layers of 27, 20 and 13.5% (Cawthorn, E. G., and Chan, C. B., Mol. Cell. Endocrinol., 75:197 (1991)). Islets were harvested mainly from the 13.5–20% interface but could also be found in the pellet. For insulin release experiments, batches of 5 islets were cultured in RPMI medium containing 11.0 mM glucose and supplemented with 1% penicillin-streptomycin, 7.5% fetal bovine serum (all from Gibco/BRL, Burlington, ON) and 10 mM Hepes (Sigma). After culturing for 20–24 h, the islets were transferred to microcentrifuge tubes, pelleted by centrifugation (800×g for 5 min) and the medium aspirated and replaced with 1.0 ml DME medium containing 1% gelatin and glucose as indicated in the Results section. After incubation at 37° C. for 90 min the islets were centrifuged as before. The supernatant was collected and stored at −4° C. until assayed. The pellet was resuspended in 3% acetic acid and stored at −4° C. Both fractions were assayed for insulin using a kit (Linco, St. Charles, Mo.) and insulin release was expressed as % of total islet content to account for variations in islet size.

Determination of ATP/ADP Levels: For determination of islet ATP/ADP, batches of 50 freshly isolated islets were centrifuged to remove isolation medium and resuspended in 500 µl phosphate buffered saline, pH 7.4. An equal volume of 12% trichloroacetic acid was added to lyse the islets and precipitate protein. After clarifying the supernatant by centrifugation (2,500×g for 10 min), 400 µl of supernatant was neutralized with 1 N KOH and divided into 4×100 µl fractions. Two fractions were incubated for 30 min at room temperature with phosphoenolpyruvate and pyruvate kinase to convert ADP to ATP. All fractions were then assayed for ATP spectrophotometrically by measuring the conversion of NADH to NAD+ in the presence of phosphoglycerate phosphokinase and glyceraldehyde phosphate dehydrogenase (Sigma), and ADP was determined by subtraction (Adra, C. N., et al., Gene, 60.:65 (1987); Li, E., et al., Proc. Natl. Acad. Sci. USA, 90:1590 (1993)).

Statistical analysis: Statistical analysis was performed using StatView 4.0 (Abacus Concept, Berkeley, Calif., USA). Results are presented as the mean+/−SE. Statistical significance was determined using either Unpaired Student t test and ANOVA analysis.

Results: Of note, total ambient pancreatic insulin content (ug insulin/pancreas ) was equal in control versus UCP2-deficient mice in the fed state (61.9+/−4.7 versus 66.5+/13.3, mean+/−SE respectively).

Figure 6A:
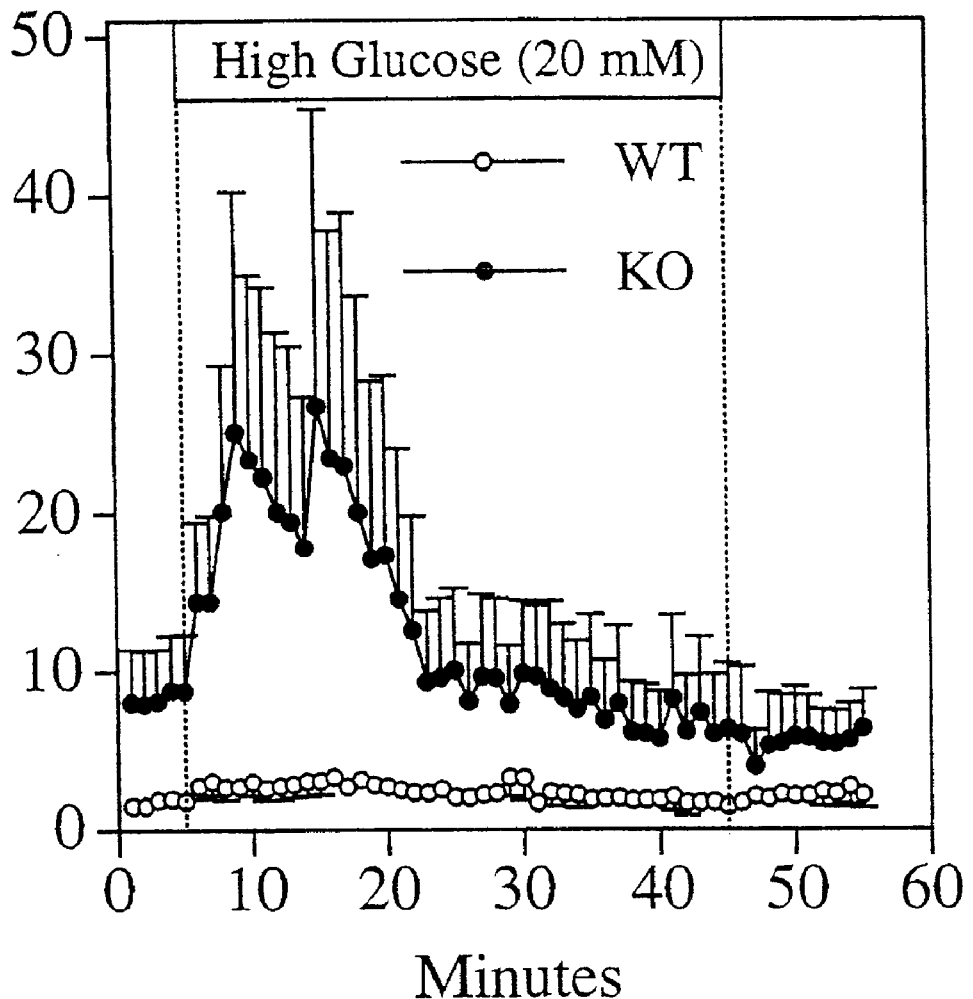
FIGS. 6A and 6B are graphic representations demonstrating insulin production by isolated perfused pancreas preparations in response to low glucose (1.4 mM) for 5 minutes; high glucose (20 mM) for 40 minutes; and low glucose for 10 minutes over a 55 minute period. The results are expressed as insulin concentration in the perfusate (ng/ml) (FIG. 6A) or as the area under the curve (FIG. 6B).
Figure 6B:
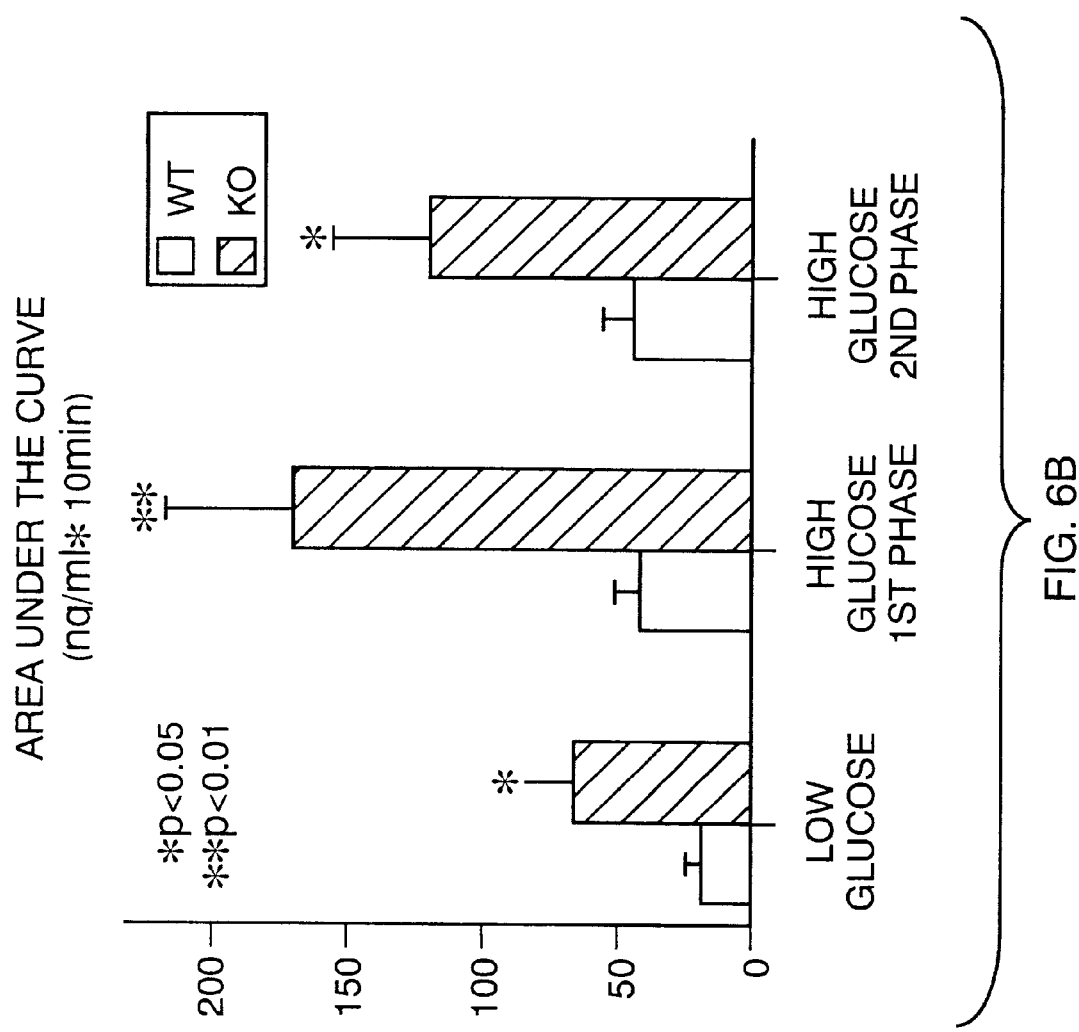

FIGS. 6A and 6B summarize data obtained from the isolated perfused pancreas studies which were performed in order to directly evaluate the glucose-responsiveness of pancreatic β-cells. Pancreas obtained from wildtype and knockout mice was perfused with LOW glucose (1.4 mM) for 5 minutes; HIGH glucose (20 mM) for 40 minutes; and LOW glucose for 10 minutes over a 55 minute period and insulin release was assessed. The results are expressed as insulin release into the perfusate (ng/ml) or as area under the curve during low glucose (first 5 minutes of perfusion), during the first 10 minutes of high glucose (1st phase) and the second 10 minutes of high glucose (2nd phase). When considered together the results indicate that in the presence of either low or high concentrations of glucose the pancreas of UCP2-deficient mice overproduced insulin. Following perfusion, total pancreatic insulin content (ug insulin/ pancreas) was equal in control versus UCP-deficient mice (72.0+/121.0 versus 68.3+/−9.7, mean+/1 SE, respectively).

Figure 7A:
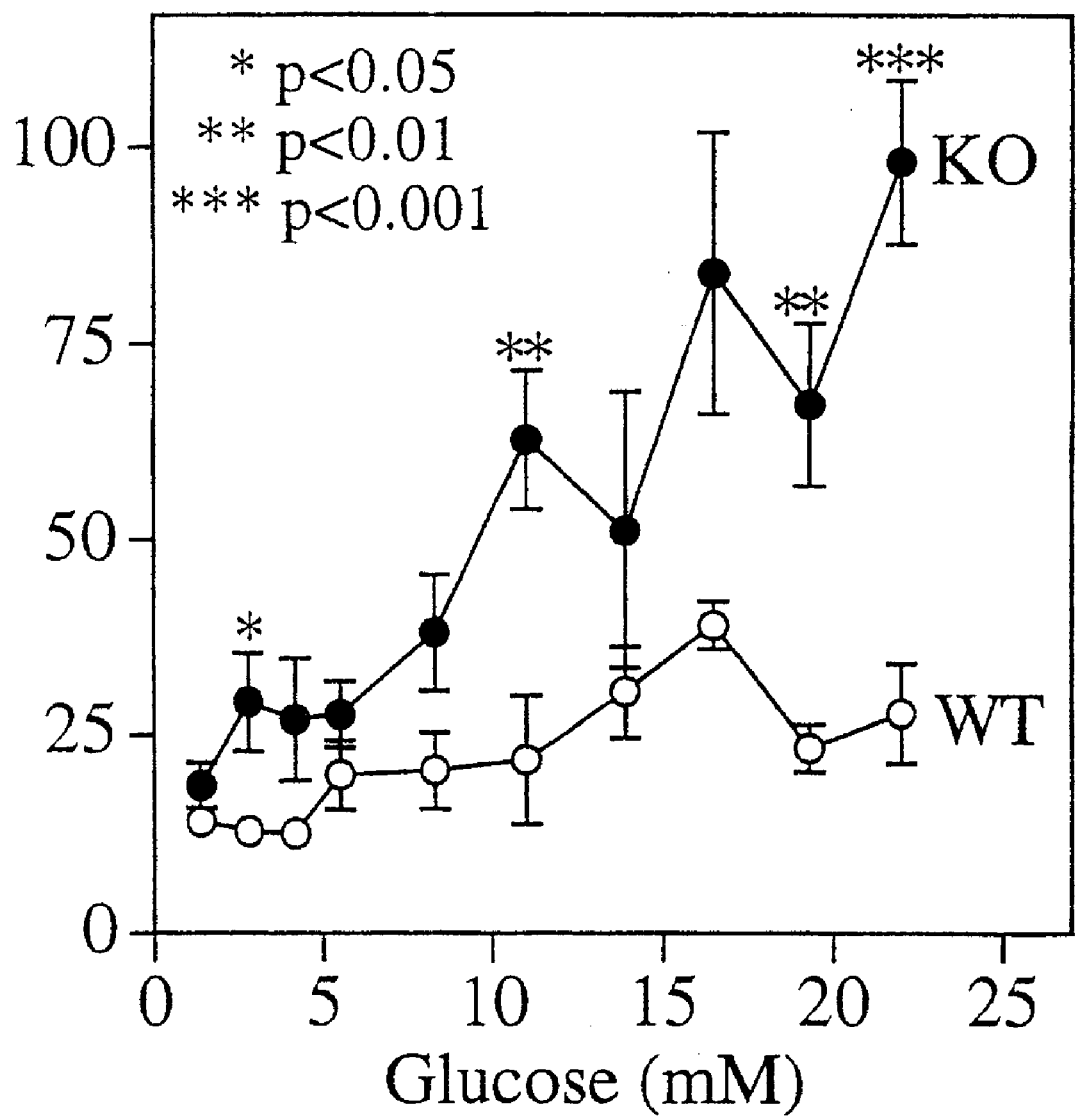
FIG. 7A is a graphic representation demonstrating in vitro insulin production by isolated pancreatic islets by wild type (+/+) and UCP2 knockout (–/–) mice in response to varying concentrations of glucose.

FIGS. 7A and 7B summarize data obtained from isolated pancreatic islet studies. Briefly, islets were exposed to varying concentrations of glucose and insulin release and in a separate study islets were exposed to 5.5 mM glucose and ATP, ADP and ATP/ADP ratios were assessed. The ATP/ADP ratio was increased in UCP2-deficient islets. Insulin level in UCP2KO mice was increased 2-fold, glucose level was deceased by 20%. Total islet insulin content (ng/islet) was not different between control and UCP2-deficient islets following incubation (1.87+/−0.20 versus 2.21+/−0.16 mean+/1 SE, respectively); however, when islets were incubated in the presence of 5.5 mM glucose, UCP2-deficient islets had lower concentrations of ADP and higher ATP/ADP ratios (FIG. 7B). The incubated islet studies confirm the observations reported above from the perfused pancreas studies by demonstrating that UCP2-deficient islets also oversecreted insulin in the presence of low, medium and high concentrations of glucose. These results are consistent with the theory that UCP2 is an important control point regulating insulin secretion.

In summary, the glucose-stimulated insulin release data presented herein demonstrate that UCP2-deficient mice cleared glucose more quickly during glucose tolerance tests (e.g., IPGTT) and secreted 3-times more insulin in response to a glucose challenge during isolated pancreatic perfusions or incubated islet studies. Considered together, the data from Examples 5 and 6 indicate that pancreatic β-cells from UCP2-deficient mice have increased responsiveness to glucose, which results in increased insulin secretion. This effect is likely due to an increased ATP/ADP ratio, which couples glucose metabolism to insulin secretion. These results indicate that UCP2 plays an important role as a negative regulator of insulin secretion and further indicate that inhibitors or UCP2 have utility as therapeutic agents for the treatment or prevention of conditions or diseases associated with UCP2, such as type 2 diabetes.

EXAMPLE 7

UCP2 Expression in Pancreatic Islets of ob/ob Mice

Both insulin resistance and β-cell dysfunction are important in the pathogenesis of type 2 diabetes. Insulin resistance, in isolation, can be compensated for by increased insulin secretion. In individuals who develop diabetes, β-cells are unable to meet the demand for increased insulin secretion, resulting in marked hyperglycemia due to a relative decrease in circulating insulin levels. In most cases, the cause of β-cell dysfunction is unknown. Of note, UCP2 mRNA expression was observed to be increased in adipose tissue of ob/ob mice (Gimeno, R. E., et al., *Diabetes* 46:900 (1997)) raising the possibility that it may be increased in their β cells as well.

In order to address this issue, pancreatic islets were isolated from control (+/+) and obese (ob/ob) mice. Blood glucose, serum insulin and pancreatic islet UCP2 mRNA levels were determined in control and ob/ob mice.

Sample Determinations: Blood and pancreatic islets were obtained from 4 control (+/+) and 4 ob/ob, 4 month old mice. Islets from each genotype were pooled and RNA was extracted for Northern blot analysis.

Figure 8A:
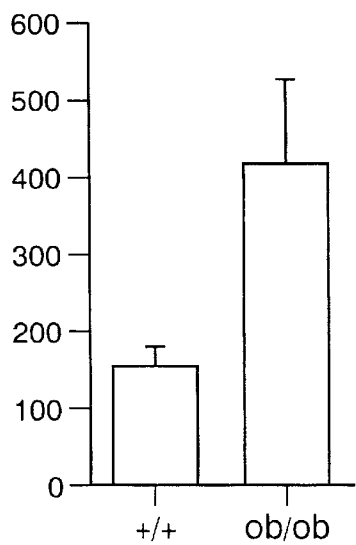
FIGS. 8A and 8B are graphic representations demonstrating the blood glucose (mg/dl) (FIG. 8A) and insulin (ng/ml) (FIG. 8B) in control and ob/ob mice. Results are expressed as mean +/–SE.
Figure 8B:
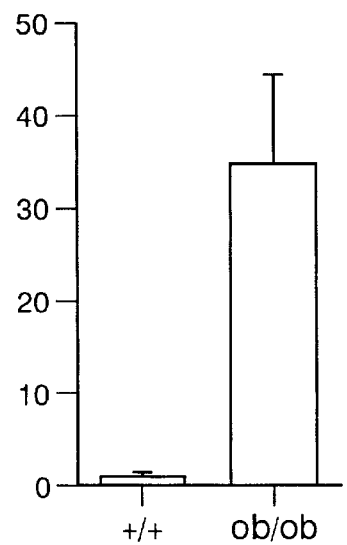

Results: Blood glucose and insulin levels are presented in FIGS. 8A and 8B as a mean +/−SE. The data indicate that blood glucose and serum insulin levels were elevated by 2.7 and 33-fold, respectively, in ob/ob mice demonstrating that although hyperinsulinemic, these animals had insulin levels that were inadequately elevated with respect to their marked hyperglycemia. The Northern results indicate that UCP2 mRNA was observed to be significantly increased in ob/ob pancreatic islets. These results indicate that UCP2 expression is elevated in a rodent model (ob/ob) of type 2 diabetes. These findings indicate that inhibitors of UCP2-mediated activity (e.g., negative regulation), may mediate an increase in insulin secretion or insulin responsiveness which offer a novel means of treating type II diabetes.

In summary, the data presented herein demonstrate that UCP2 expressed at endogenous (e.g, physiologic) levels in pancreatic β-cells negatively regulates insulin secretion.

While this invention has been particularly shown and described with references to preferred embodiments thereof, it will be understood by those skilled in the art that various changes in form and details may be made therein without departing from the scope of the invention encompassed by the appended claims.

We claim:

1. A transgenic mouse whose genome comprises a disruption of the UCP2 gene such that the mouse lacks or has reduced levels of functional UCP2 protein, and wherein said mouse releases an increased level of insulin in response to glucose stimulation relative to the amount of insulin released by a wild-type mouse in response to said glucose stimulation.

2. The transgenic mouse of claim 1, wherein the genome comprises a disruption of the UCP2 gene selected from the group consisting of: a homozygous disruption and a heterozygous disruption.

3. The transgenic mouse of claim 2, wherein the disruption of the UCP2 gene is in a segment between introns 2 and 7 of the UCP2 gene.

4. The transgenic mouse of claim 2, wherein the disruption of the UCP2 gene comprises a substitution of an exon of said UCP2 gene with an exogenous nucleic acid sequence.

5. Cultured cells isolated from the mouse of claim 1, wherein the genomes of said cells comprise a disruption of the UCP2 gene and said cells lack or have reduced levels of functional UCP2 protein.

6. Cultured pancreatic cells isolated from the mouse of claim 1, wherein the genomes of said cells comprise a disruption of the UCP2 gene and said cells lack or have reduced levels of functional UCP2 protein.

7. A method of producing a transgenic mouse whose genome comprises a disruption of the UCP2 gene such that the mouse lacks or has reduced levels of functional UCP2 protein, and wherein said mouse releases an increased level of insulin in response to glucose stimulation relative to the amount of insulin released by a wild-type mouse in response to said glucose stimulation, said method comprising:

a) introducing a targeting vector which disrupts the UCP2 gene in a mouse embryonic stem cell, thereby producing a transgenic embryonic stem cell with the disrupted UCP2 gene;
 b) selecting the transgenic embryonic stem cell whose genome comprises the disrupted UCP2 gene;
 c) introducing the transgenic embryonic stem cell in b) into a blastocyst, thereby forming a chimeric blastocyst; and
 d) introducing the chimeric blastocyst of c) into the uterus of a pseudopregnant mouse;
 wherein said pseudopregnant mouse gives birth to a transgenic mouse whose genome comprises a disruption of the UCP2 gene such that the mouse lacks or has reduced levels of functional UCP2 protein, and wherein said mouse releases an increased level of insulin in response to glucose stimulation relative to the amount of insulin released by a wild-type mouse in response to said glucose stimulation.

8. The method of claim 7 further comprising:

e) breeding the transgenic mouse with a second mouse to generate F1 progeny having a heterozygous disruption of the UCP2 gene, thereby expanding the population of mice having a heterozygous disruption of the UCP2 gene; and
 d) crossbreeding the F1 progeny to produce a transgenic mouse which lacks a functional UCP2 gene due to a homozygous disruption of the UCP2 gene.

9. The method of claim 7, wherein the genome of said transgenic mouse comprises a disruption of the UCP2 gene selected from the group consisting of: a homozygous disruption and a heterozygous disruption.

10. A method for determining whether an agent inhibits UCP2 activity, said method comprising:

a)
  i) administering an amount of glucose sufficient to stimulate insulin production and the agent to a mouse, whose genome comprises the wild type UCP2 gene;
  ii) administering an amount of glucose sufficient to stimulate insulin production and the agent to a transgenic mouse, whose genome comprises a disruption of the UCP2 gene such that the mouse lacks functional UCP2 protein, and wherein said mouse releases an increased level of insulin in response to glucose stimulation relative to the amount of insulin released by a wild-type mouse in response to said glucose stimulation;
  iii) administering an amount of glucose sufficient to stimulate insulin production to a mouse whose genome comprises the wild type UCP2 gene; and
  iv) administering an amount of glucose sufficient to stimulate insulin production to a transgenic mouse, whose genome comprises a disruption of the UCP2 gene such that the mouse lacks functional UCP2 protein, and wherein said mouse releases an increased level of insulin in response to glucose stimulation relative to the amount of insulin released by a wild-type mouse in response to said glucose stimulation;
 b) measuring insulin levels of the mouse of a) i), the mouse of a) iii), the transgenic mouse of a) ii) and the trangenic mouse of a) iv);
 c) comparing the insulin level produced by the mouse of a) i) to the insulin level produced by the mouse of a) iii); and d) comparing the insulin level produced by the mouse of a) ii) to the insulin level produced by the mouse of a) iv);

wherein if the insulin level of the mouse of a) i) is increased compared to the insulin level of the mouse of a) iii), and the insulin level of the mouse of a) ii) is about the same as the insulin level of the mouse of a) iv), then the agent inhibits UCP2.

11. The method of claim 10, wherein the genome of the transgenic mouse of a) ii) and the genome of the transgenic mouse of a) iv) comprise a disruption in a segment between introns 2 and 7 of the UCP2 gene.

12. The method of claim 11, wherein the genome of the transgenic mouse of a) ii) and the genome of the transgenic mouse of a) iv) comprise a selectable marker expression cassette replacing a segment between introns 2 and 7 of the UCP2 gene.

13. A method for identifying an agent which exhibits UCP2 activity comprising:
   a) introducing the agent into pancreatic β-cells of a transgenic mouse whose genome comprises a disruption of the UCP2 gene such that the mouse lacks or has reduced levels of functional UCP2 protein, and wherein said mouse releases an increased level of insulin in response to glucose stimulation relative to the amount of insulin released by a wild-type mouse in response to said glucose stimulation; and
   b) determining whether a decrease in insulin responsiveness to glucose responsiveness occurs in said cells; wherein if a decrease in insulin responsiveness to glucose occurs in the cells of the transgenic mouse in the presence of the agent, then the agent exhibits UCP2 activity.

14. The method of claim 13, wherein the genome of the transgenic mouse comprises a disruption of the UCP2 gene selected from the group consisting of: a homozygous disruption and a heterozygous disruption.

15. A method of identifying an agent which exhibits UCP2 activity comprising:
   a) introducing the agent into a transgenic mouse whose genome comprises a disruption of the UCP2 gene such that the mouse lacks or has reduced levels of functional UCP2 protein, and wherein said mouse releases an increased level of insulin in response to glucose stimulation relative to the amount of insulin released by a wild-type mouse in response to said glucose stimulation; and
   b) determining whether a decrease in insulin responsiveness to glucose stimulation occurs in said mouse;

wherein if the decrease in insulin responsiveness to glucose stimulation occurs in the transgenic mouse in the presence of the agent, then the agent exhibits UCP2 activity.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: unknown
<220> FEATURE:
<223> OTHER INFORMATION: Synthetic sequence

<400> SEQUENCE: 1
cctccactca tgatctatag atc                                                23

<210> SEQ ID NO 2
<211> LENGTH: 23
<212> TYPE: DNA
<213> ORGANISM: unknown
<220> FEATURE:
<223> OTHER INFORMATION: Synthetic sequence

```
<400> SEQUENCE: 2
accctctgtc gccaccatag tca                                    23

<210> SEQ ID NO 3
<211> LENGTH: 18
<212> TYPE: DNA
<213> ORGANISM: unknown
<220> FEATURE:
<223> OTHER INFORMATION: Synthetic sequence

<400> SEQUENCE: 3
gcactgcggc ctgttttg                                          18
```